United States Patent
Lin et al.

(10) Patent No.: US 8,906,048 B2
(45) Date of Patent: Dec. 9, 2014

(54) MODULAR VESSEL HARVESTING SYSTEM AND METHOD

(75) Inventors: Arthur M. Lin, Fremont, CA (US); Joseph N. Lamberti, Castro Valley, CA (US); Kenny Dang, San Jose, CA (US); Michael C. Stewart, San Jose, CA (US); Charles J. Adam, San Jose, CA (US); Justin N. Williams, San Jose, CA (US)

(73) Assignee: MAQUET Cardiovascular LLC, Mahwah, NJ (US)

( * ) Notice: Subject to any disclaimer, the term of this patent is extended or adjusted under 35 U.S.C. 154(b) by 376 days.

(21) Appl. No.: 13/027,205

(22) Filed: Feb. 14, 2011

(65) Prior Publication Data

US 2012/0046677 A1    Feb. 23, 2012

Related U.S. Application Data

(63) Continuation of application No. 10/951,426, filed on Sep. 28, 2004, now Pat. No. 7,887,558.

(51) Int. Cl.
| | |
|---|---|
| A61B 17/22 | (2006.01) |
| A61B 18/14 | (2006.01) |
| A61B 17/00 | (2006.01) |
| A61B 17/34 | (2006.01) |
| A61B 17/32 | (2006.01) |

(52) U.S. Cl.
CPC ........... *A61B 17/00008* (2013.01); *A61B 18/14* (2013.01); *A61B 2017/00969* (2013.01); *A61B 2017/3419* (2013.01); *A61B 2017/320044* (2013.01); *A61B 2017/00367* (2013.01); *A61B 2017/3445* (2013.01)
USPC ............................................ 606/159; 600/36

(58) Field of Classification Search
USPC ............ 606/159, 169, 170, 190; 600/36, 104, 600/106
See application file for complete search history.

(56) References Cited

U.S. PATENT DOCUMENTS

| | | | |
|---|---|---|---|
| 4,370,980 | A | 2/1983 | Lottick |
| 5,254,117 | A | 10/1993 | Rigby et al. |
| 5,258,006 | A | 11/1993 | Rydell et al. |
| 5,374,277 | A | 12/1994 | Hassler et al. |
| 5,381,943 | A | 1/1995 | Allen et al. |

(Continued)

OTHER PUBLICATIONS

Guidant, "A Guide to: Vasoview.RTM. 5 EVH System" Product Brochure, 2002, Guidant Corp., Santa Clara, CA (glossy 6-sided brochure). cited by other.

(Continued)

*Primary Examiner* — Victor Nguyen

(57) ABSTRACT

A vessel harvesting system that is suitable for harvesting target vessels such as the saphenous vein or radial artery for cardiac artery bypass graft surgery. The system includes a vessel harvesting tool with an elongated cannula and a plurality of surgical instruments therein for separating the target vessels from the surrounding tissue and side branches. The harvesting tool includes a modular handle unit with a base attached to the elongated cannula and a sled that can adapt the base to various types of vessel severing/securing tools, such as tissue welders, bipolar scissors, and bipolar bisectors. The handle unit may be relatively rigid and integrated with the various tool movement controls to facilitate one-handed operation by a user. A severing/securing tool rotation mechanism may be incorporated within the handle and operated by a thumbwheel or other such mechanism. The vessel harvesting system may also provide distal $CO_2$ insufflation for enhanced maintenance of the operating cavity.

20 Claims, 26 Drawing Sheets

(56) References Cited

U.S. PATENT DOCUMENTS

| | | | |
|---|---|---|---|
| 5,480,409 | A | 1/1996 | Riza |
| 5,577,654 | A | 11/1996 | Bishop |
| 5,588,580 | A | 12/1996 | Paul et al. |
| 5,588,581 | A | 12/1996 | Conlon et al. |
| 5,601,224 | A | 2/1997 | Bishop et al. |
| 5,607,095 | A | 3/1997 | Smith et al. |
| 5,609,601 | A | 3/1997 | Kolesa et al. |
| 5,626,587 | A | 5/1997 | Bishop et al. |
| 5,634,584 | A | 6/1997 | Okorocha et al. |
| 5,643,294 | A | 7/1997 | Tovey et al. |
| 5,662,662 | A | 9/1997 | Bishop et al. |
| 5,743,456 | A | 4/1998 | Jones et al. |
| 5,797,536 | A | 8/1998 | Smith et al. |
| 5,817,109 | A | 10/1998 | McGarry et al. |
| 5,827,279 | A | 10/1998 | Hughett et al. |
| 5,829,662 | A | 11/1998 | Allen et al. |
| 5,830,231 | A | 11/1998 | Geiges, Jr. |
| RE36,043 | E | 1/1999 | Knighton |
| 5,868,785 | A | 2/1999 | Tal et al. |
| 5,873,886 | A | 2/1999 | Larsen et al. |
| 5,895,353 | A | 4/1999 | Lunsford et al. |
| 5,928,138 | A | 7/1999 | Knight et al. |
| 5,931,848 | A | 8/1999 | Saadat |
| 5,931,849 | A | 8/1999 | Desvignes et al. |
| 5,993,470 | A | 11/1999 | Yoon |
| 6,066,117 | A | 5/2000 | Fox et al. |
| 6,162,173 | A | 12/2000 | Chin et al. |
| 6,171,316 | B1 | 1/2001 | Kovac et al. |
| 6,176,825 | B1 | 1/2001 | Chin et al. |
| 6,342,058 | B1 | 1/2002 | Portney |
| 6,406,425 | B1 * | 6/2002 | Chin et al. .............. 600/205 |
| 6,451,017 | B1 | 9/2002 | Moutafis et al. |
| 6,458,124 | B1 | 10/2002 | Garito et al. |
| 6,471,638 | B1 | 10/2002 | Chang et al. |
| 6,500,115 | B2 | 12/2002 | Krattiger et al. |
| 6,540,737 | B2 | 4/2003 | Bacher et al. |
| 6,540,764 | B1 | 4/2003 | Kieturakis et al. |
| 6,592,582 | B2 | 7/2003 | Hess et al. |
| 6,660,016 | B2 | 12/2003 | Lindsay |
| 6,830,546 | B1 | 12/2004 | Chin et al. |
| 7,485,092 | B1 * | 2/2009 | Stewart et al. .............. 600/127 |
| 7,534,243 | B1 | 5/2009 | Chin et al. |
| 7,695,470 | B1 | 4/2010 | Stewart et al. |
| 7,867,163 | B2 | 1/2011 | Chin et al. |
| 7,887,558 | B2 | 2/2011 | Lin et al. |
| 7,938,842 | B1 | 5/2011 | Chin et al. |
| 8,241,210 | B2 | 8/2012 | Lunsford et al. |

OTHER PUBLICATIONS

Guidant, "A Guide to: Vasoview.RTM. Uniport.RTM. Plus EVH System" Product Brochure, 2003, Guidant Corp., Santa Clara, CA (glossy 2-sided brochure). cited by other.

Guidant, "Vasoview.RTM. 5 Harvesting Cannula Single-Use" Instructions for Use, 2003, Guidant Corp., Santa Clara, CA (4 sheets). cited by other.

Guidant, "Vasoview.RTM. Bisector—Flexible Endoscopic 5mm Bipolar Forceps" Product Insert, 2000, Guidant Corp., Santa Clara, CA (1 sheet). cited by other.

Guidant, "Vasoview.RTM. Bipolar Scissors—Flexible Endoscopic 5mm Bipoiar Scissors" Product Insert, 2000, Guidant Corp., Santa Clara, CA (1 sheet). cited by other.

* cited by examiner

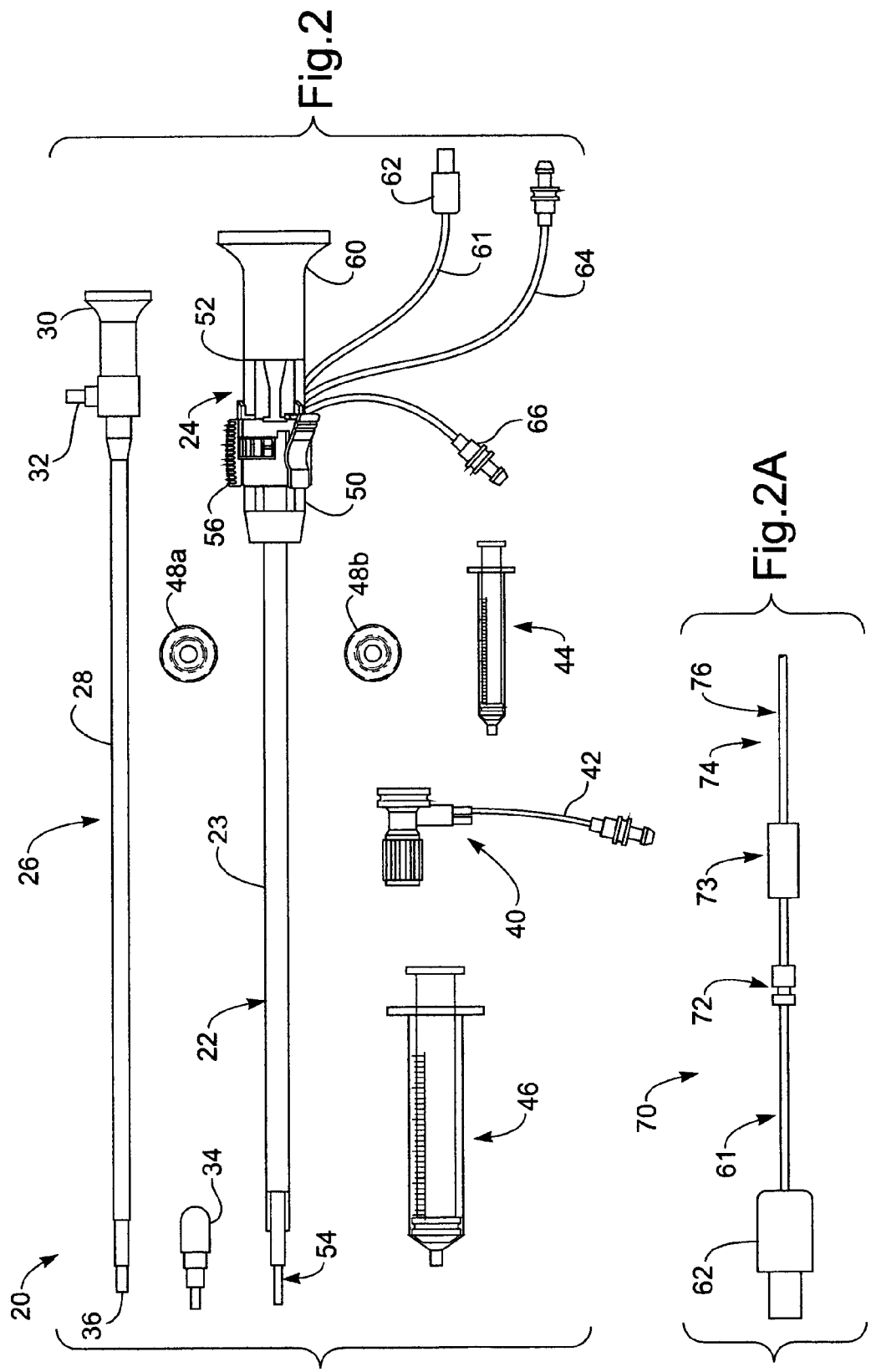

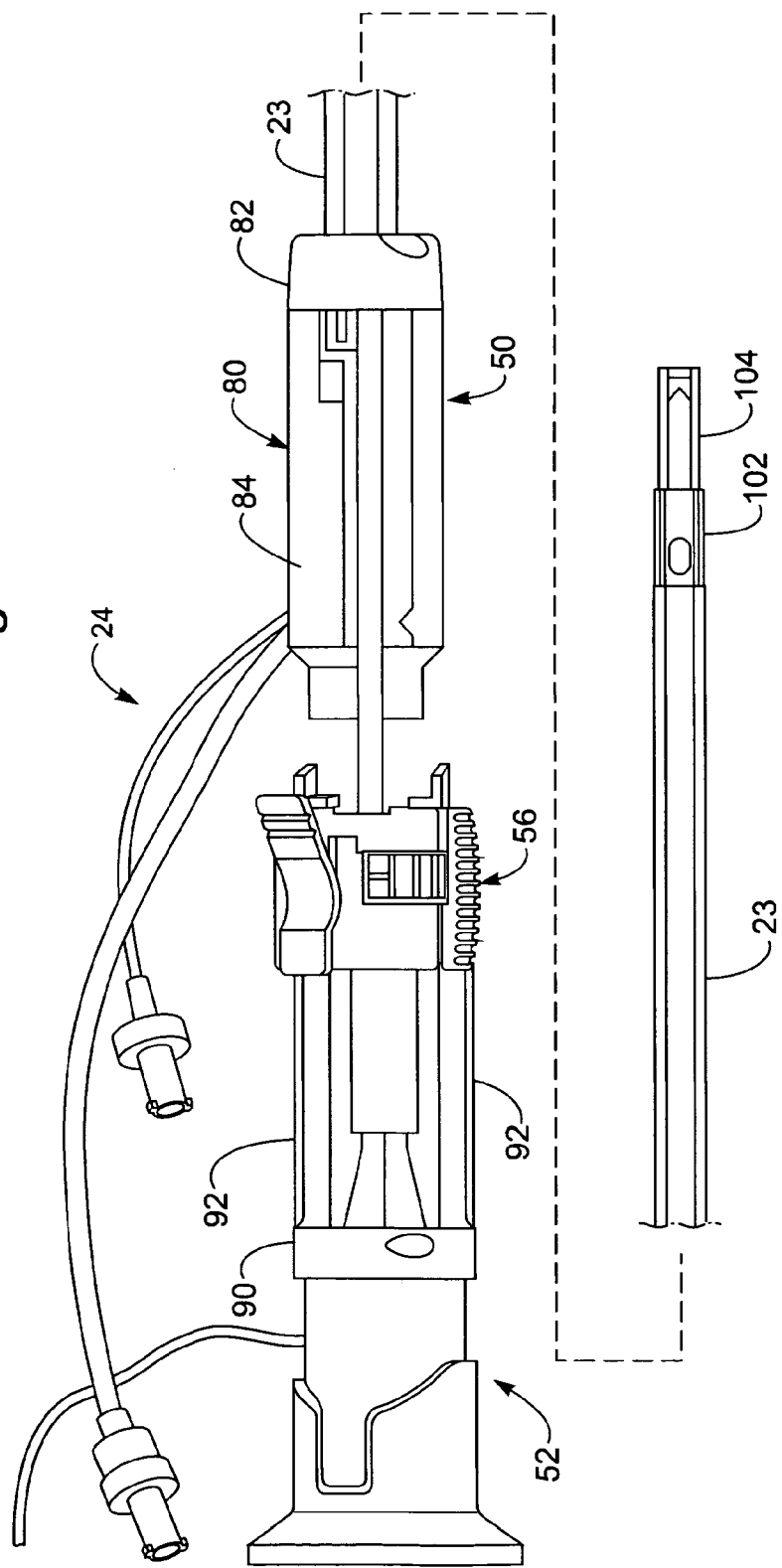

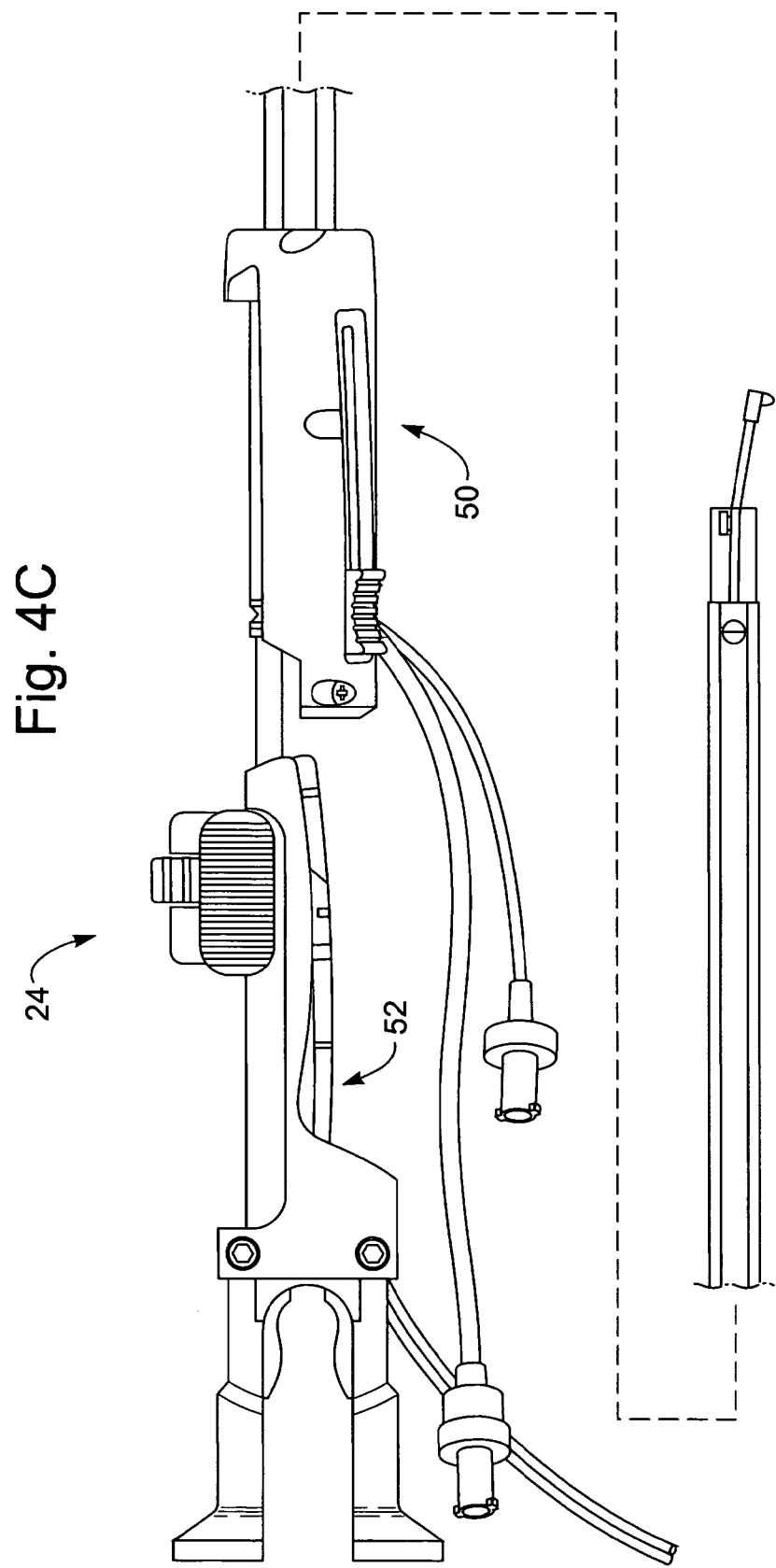

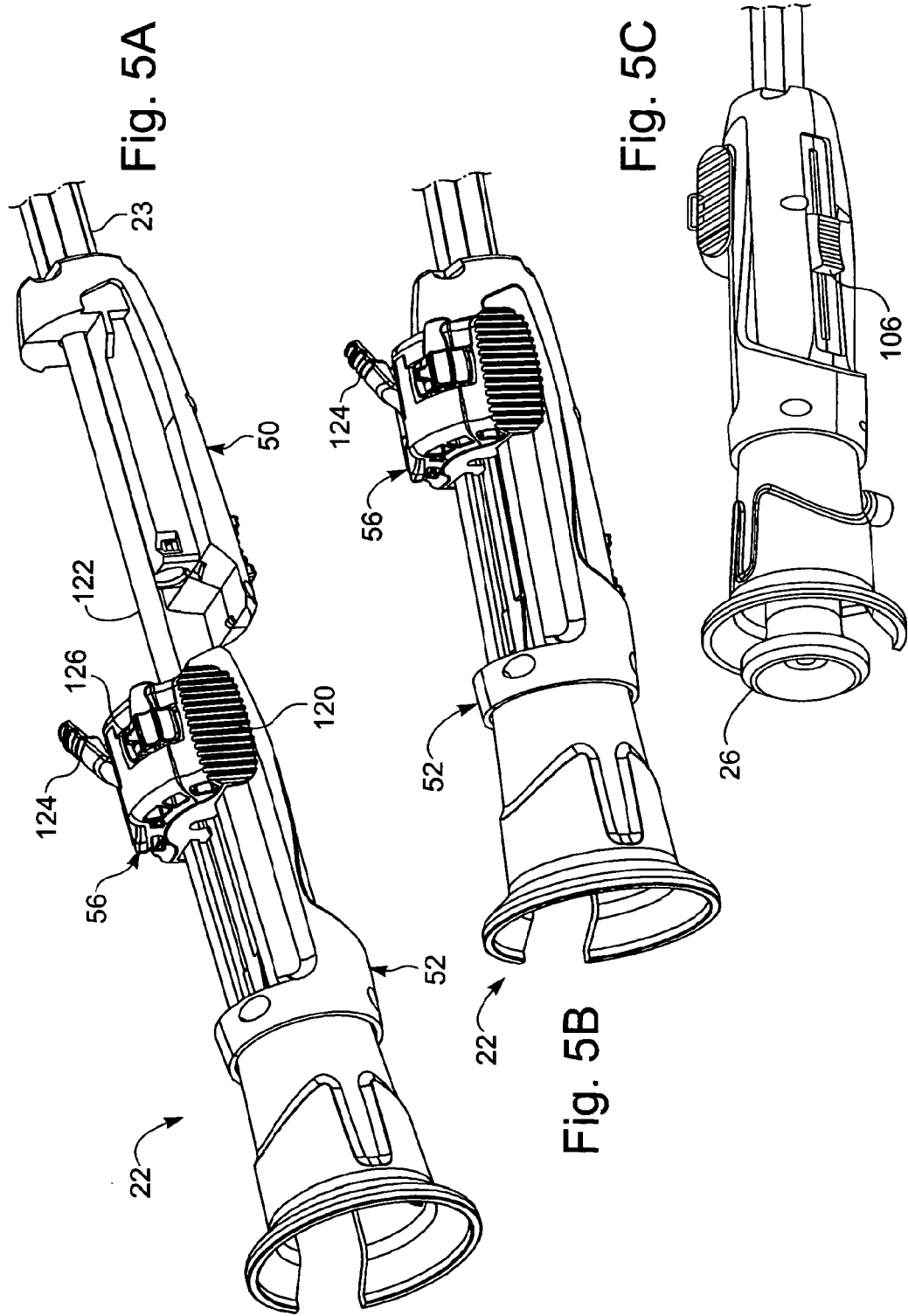

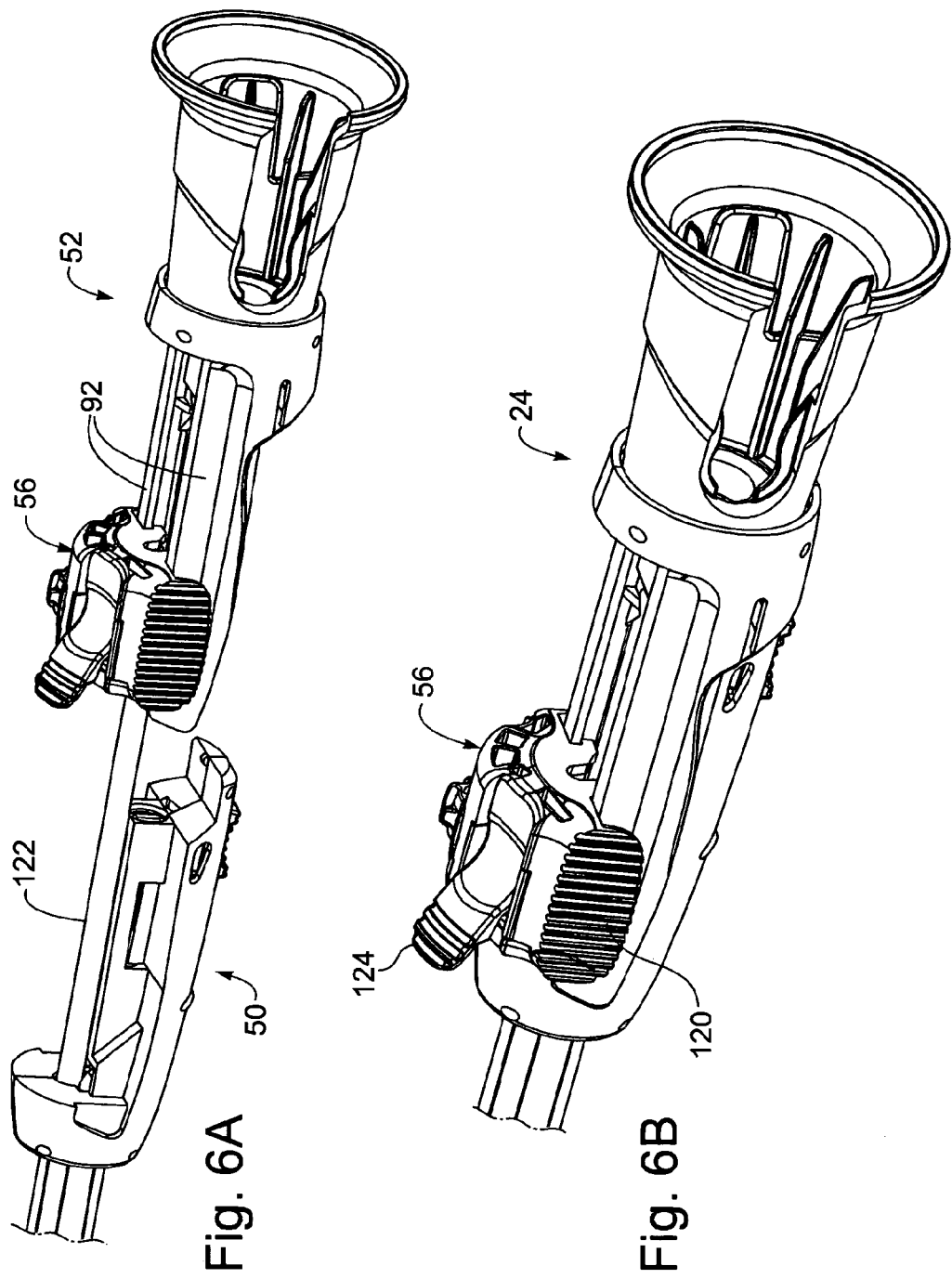

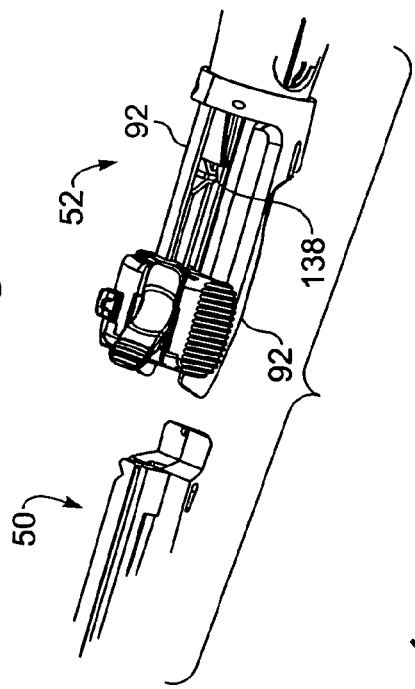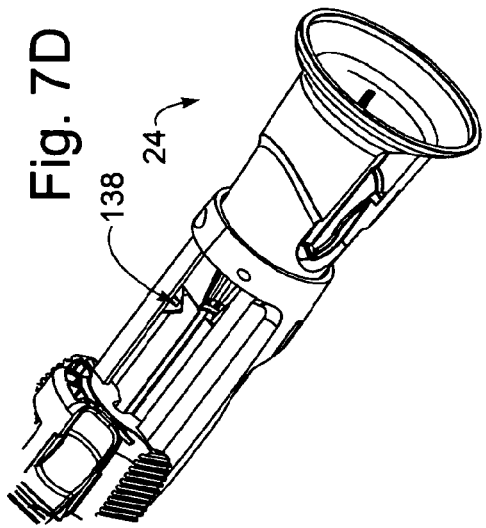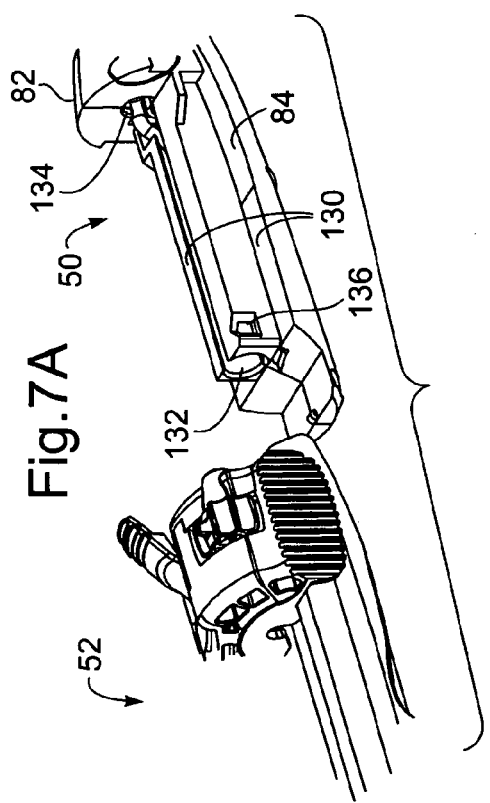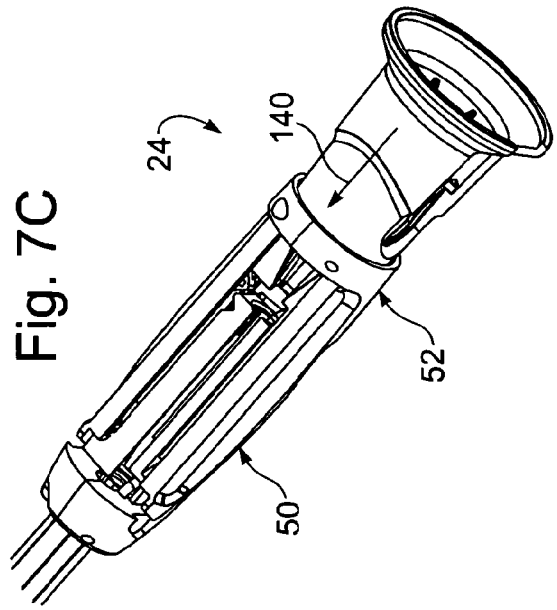

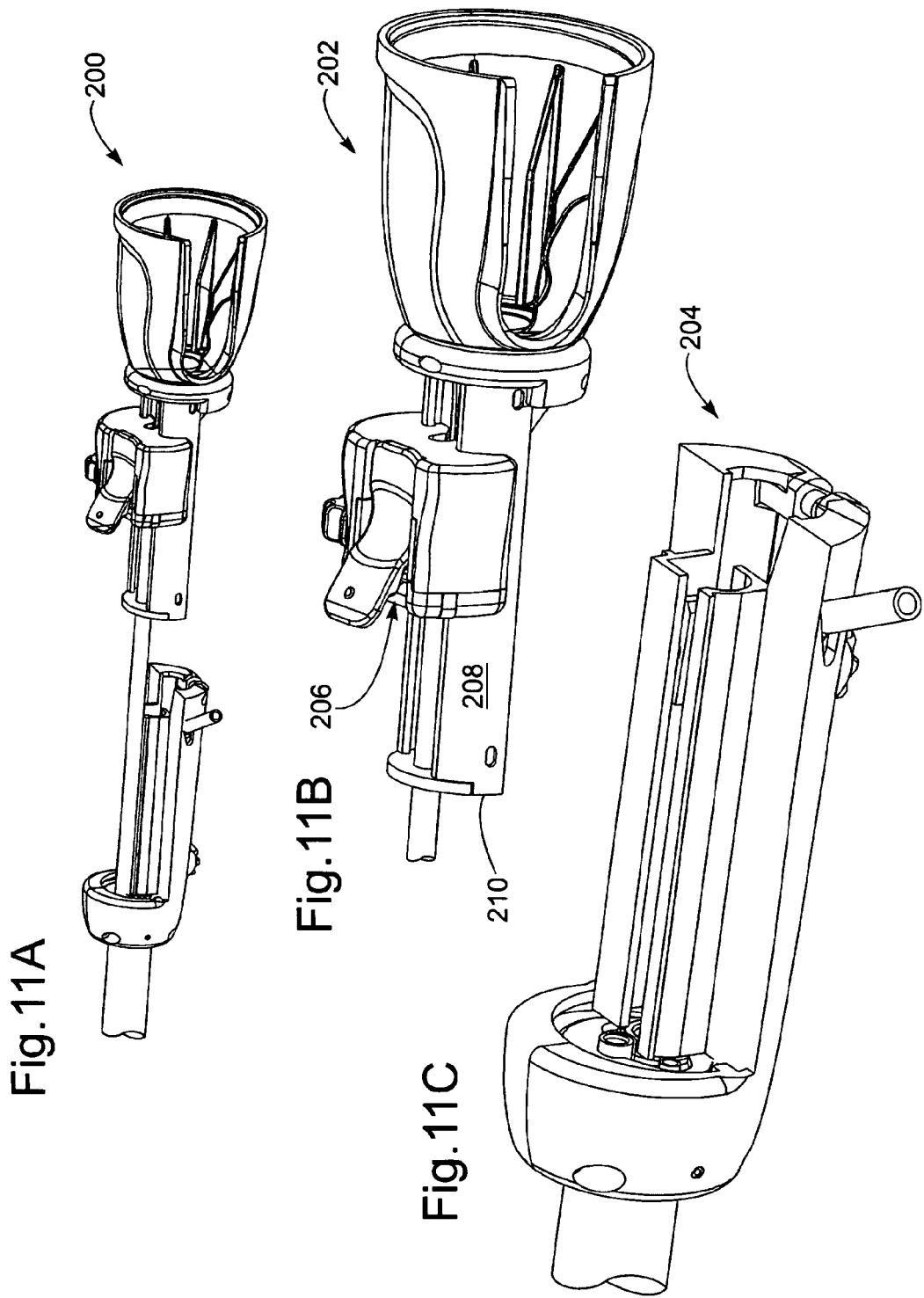

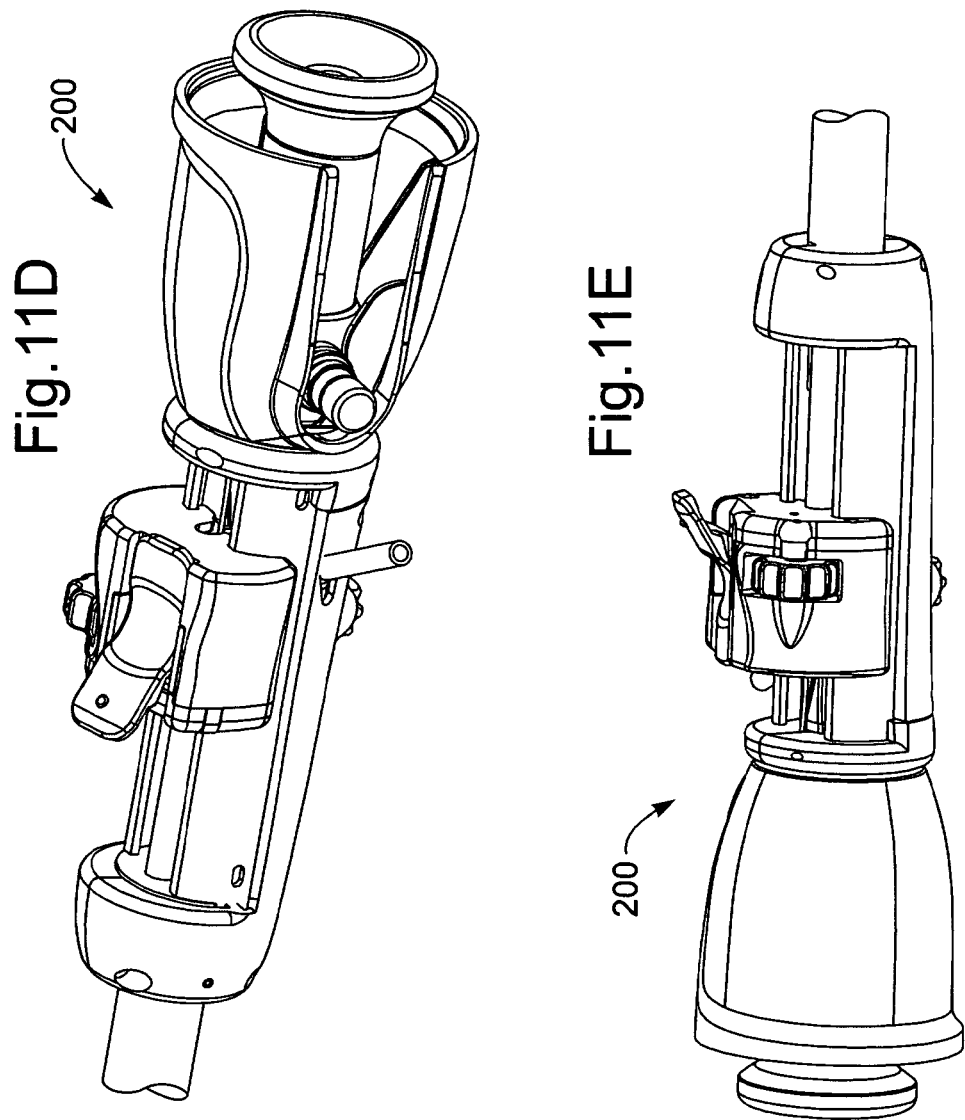

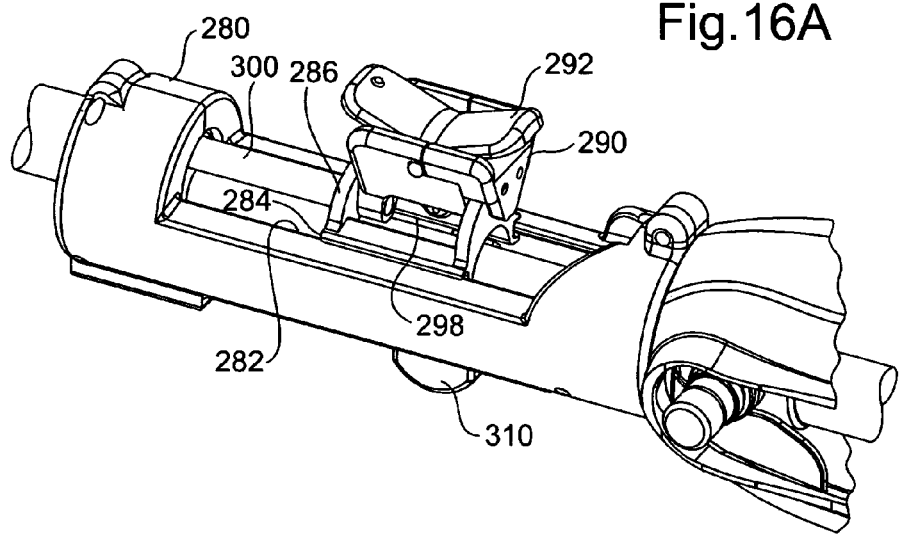
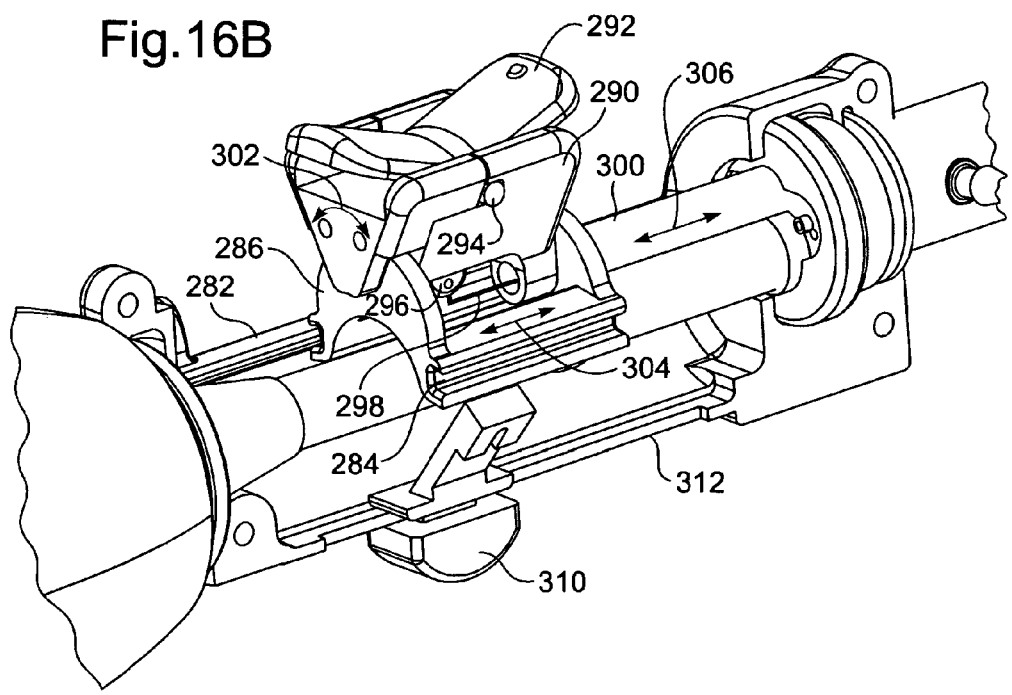

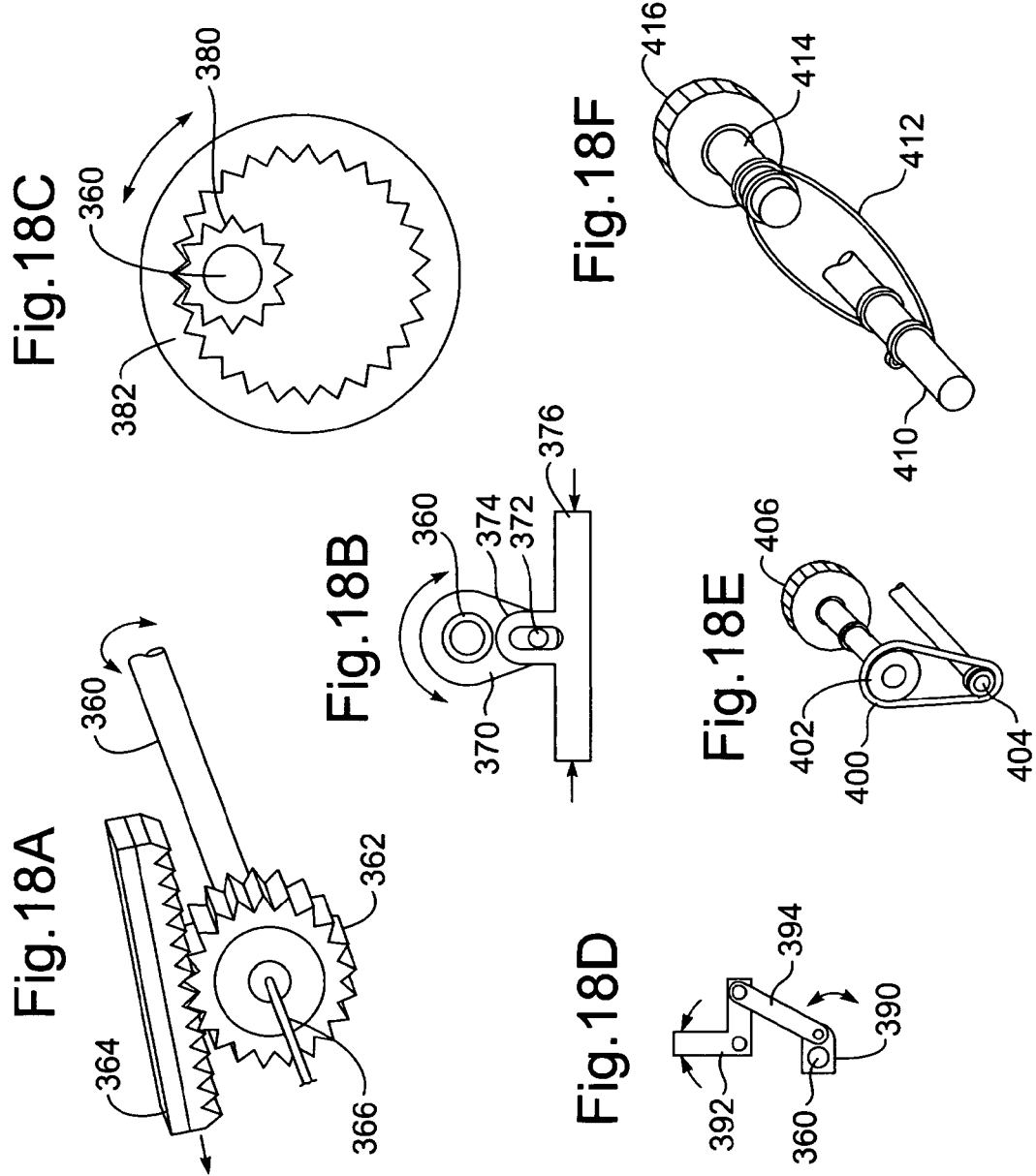

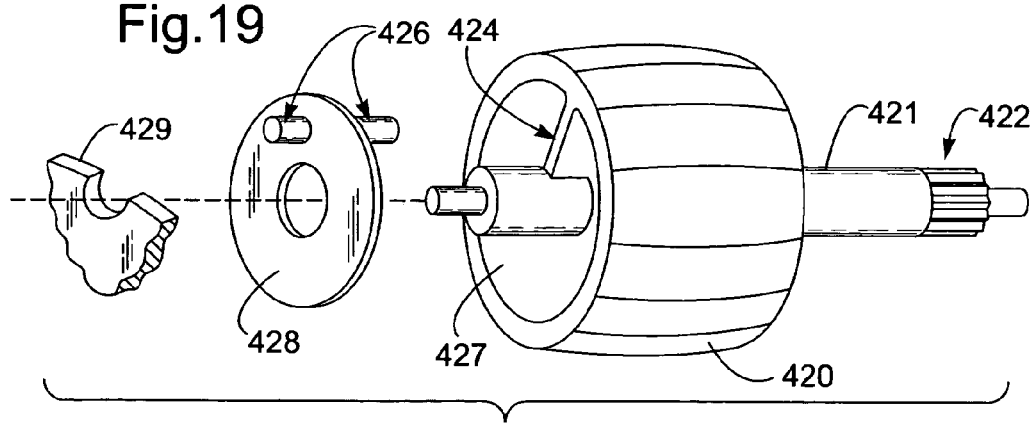
Fig. 19
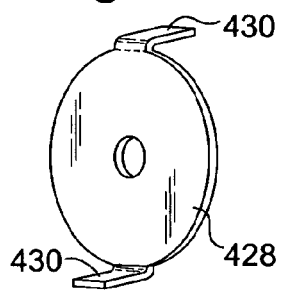
Fig. 19A
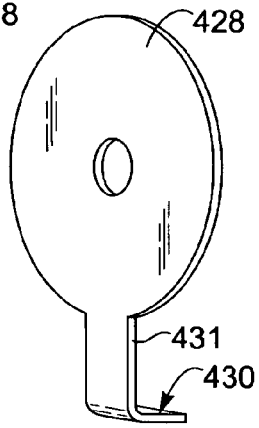
Fig. 19C
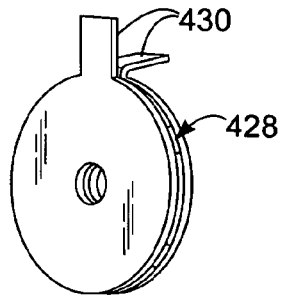
Fig. 19D
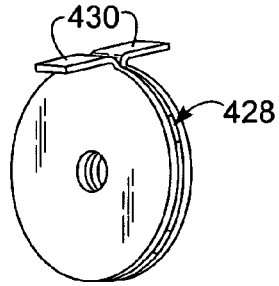
Fig. 19E
Fig. 19B
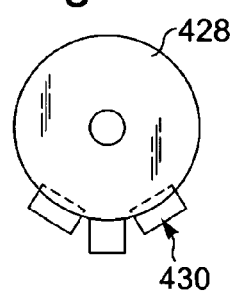
Fig. 19F
Fig. 19G
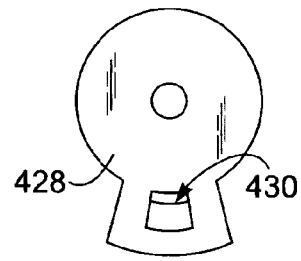
Fig. 19H
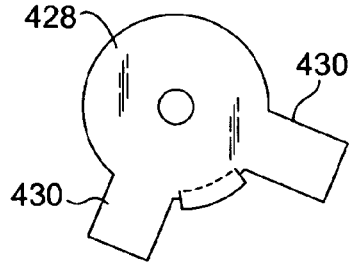

MODULAR VESSEL HARVESTING SYSTEM AND METHOD

RELATED APPLICATION DATA

The application is a continuation of U.S. patent application Ser. No. 10/951,426, filed on Sep. 28, 2004, pending, the entire disclosure of which is expressly incorporated by reference herein.

FIELD OF THE INVENTION

The present invention relates to surgical devices and methods for dissection and removal of blood vessels from a patient's body and, in particular, to endoscopic vessel harvesting devices and methods.

BACKGROUND OF THE INVENTION

Endoscopic harvesting of vessels is well known in the surgical field and has been the subject of a great deal of recent technological advancement. Typically, the harvesting of vessels is performed so that the vessels can be then used for procedures such as Coronary Artery Bypass Grafting (CABG). In this procedure the saphenous veins of the legs are harvested for subsequent use in the CABG surgery. Vessel harvesting involves liberating the vessel from surrounding tissue and transecting smaller side branches, tying or ligating the vessel at a proximal site and a distal site, and then transecting the vessel at both sites before it is removed from the body.

Known endoscopic methods and devices for performing vessel harvesting are discussed in detail in U.S. Pat. No. 6,176,895 to Chin, et al., U.S. Pat. No. Re 36,043 to Knighton, U.S. Pat. No. 6,406,425 to Chin, et al., and U.S. Pat. No. 6,471,638 to Chang, et al., all of which are expressly incorporated herein by reference. Furthermore, various devices and methods disclosed in U.S. Pat. Nos. 5,895,353 to Lunsford, et al., and U.S. Pat. No. 6,162,173 to Chin, et al., and pending patent application Ser. No. 10/602,490 entitled "Apparatus and Method for Integrated Vessel Ligator and Transector" are also expressly incorporated herein by reference. Also, commercial vessel harvesting systems sold under the tradename VASOVIEW® 4 and VASOVIEW® 5 are available from Guidant Corporation of Santa Clara, Ca.

A first step in a known endoscopic method for removal of a vessel section is shown in FIGS. 1A and 1B using an optical vessel dissector 10, such as the CLEARGLIDE™ Optical Vessel Dissector sold by Ethicon, Inc. of Somerville, N.J, a subsidiary of Johnson & Johnson. The optical vessel dissector 10 is used to create an operative cavity in extraperitoneal spaces such as the retroperitoneal, preperitoneal, and subcutaneous areas, in particular surrounding vessels to be harvested. The optical vessel dissector 10 includes a cannula 12, a handle 14, and a transparent, blunt tip 16 that dissects tissue and creates a cavity for passage of the cannula 12. The device is used in conjunction with a separate endoscope for visualization through the tip during insertion, tunneling, and dissection.

Initially an incision I is made and the vessel V is located, for example the saphenous vein as illustrated. The vessel V is then dissected from the surrounding tissue using the leading edge of the optical vessel dissector 10 to separate the tissue from the vessel V, while being careful to avoid avulsion of side branches SB. At this time sufficient space is created around the vessel V so that other specific-function tools can be inserted into the incision I via lumen(s) or guides associated with the dissector 10. These tools include vessel transectors for performing a more complete severing of the vessel V which is to be removed. Severing/transecting tools (e.g., laparoscopic scissors) transect both the side branch vessels SB and the vessel V which is to be removed. Cauterizing/ligation tools (e.g., bipolar scissors) secure or close off both the side branch vessels SB and the vessel V which is to be removed. Another ligation method involves the use of a long, endoscopic clip applier that positions and applies clips at the proximal and distal ends of the vessel. Some tools perform both transection and ligation or cauterization. Ultimately, the vessel V is freed from surrounding tissue and side branches and can be transected at a desired length and removed from the cavity, sometimes within the cannula 12. The procedure may require a second incision at a distance from the first incision I to facilitate the final transection.

In some prior art systems for performing vessel harvesting, the various tools to be used to separate surrounding tissue from the vessel and sever and ligate or otherwise close off side branches are all separately provided and inserted through or alongside a primary endoscopic cannula. Each of the tools must be manipulated from a proximal end outside the body, which can be relatively cumbersome and complicated, especially since each of those tools usually has its own handle on the proximal end which in operation is placed within the same general space where the proximal handle of the primary endoscopic cannula is located. For example, FIGS. 3, 11, and 12 of U.S. Pat. No. 5,928,138 to Knight, et al. illustrate a separate ligating device 40 and cutting device 50 that are inserted into a subcutaneous cavity adjacent to a dissecting device and have separate handles for proximal manipulation. To rotate the distal tips of these devices, the entire handles must be rotated, typically by a second hand of the surgeon. This manipulation in a potentially crowded space may add difficulty to the procedure, somewhat like dueling swords.

Despite accepted endoscopic vessel harvesting systems and techniques, there remains a need for an improved device that eliminates the cumbersome nature of having to use multiple single-function tools.

SUMMARY OF THE INVENTION

The present invention provides a minimally invasive vessel harvesting system suitable for harvesting various target vessels that allows for simple and convenient operation in a limited space; easy rotation, orientation and manipulation of various tools without the need to rotate the entire handle; and provides an advantage of modular design where various functional tools could be easily and conveniently combined and interchanged in a single easy to hold unit. The system includes a vessel harvesting tool with an elongated cannula and a plurality of surgical instruments therein for separating the target vessels from the surrounding tissue and side branches. The harvesting tool has a modular handle unit with a base attached to the elongated cannula and a sled that can adapt the base to various types of vessel severing/securing tools, such as tissue welders, bipolar scissors, bisectors and the like. The handle unit may be relatively rigid and integrated with many of the various tool controls, to facilitate easy operation by a user, for example the side branch severing/securing controls and/or vessel cradle tool controls may be operated with one hand, if desired. The sled attaches or locks to the base to form a single handle unit. One exemplary sled or adapter allows the use of two handle, flexible shaft tools within a single handle modular exchangeable tool system. The adapter also may convert a single handle vessel harvesting device to a two handle vessel harvesting device with increased tool extension and maneuverability. The present invention thus provides the ability to switch between a single-handle integrated tool and a two-handle tool through the use of a modular adapter. The combination of tool modularity along with a single ergonomic handle facilitates easier learning for new customers as well as retaining the features preferred by experienced users.

A severing/securing tool rotation mechanism may be incorporated within the handle and operated by a thumbwheel, lever, toggle or other such mechanism. The angle of rotation of the thumbwheel may be either amplified or reduced depending on the particular mechanical coupling with the severing/securing tool. The vessel harvesting system may also provide distal $CO_2$ insufflation for enhanced maintenance of the operating cavity.

BRIEF DESCRIPTION OF THE DRAWINGS

FIG. 2 is an exploded view of a kit of surgical devices including a vessel harvesting system of the present invention;

FIG. 2A is a plan view of a one-piece electrical connection assembly for the vessel harvesting system of FIG. 2 with an integrated strain relief and wire interconnect;

FIGS. 4A-4F are elevational, plan, and sectional views of the vessel harvesting system of the present invention shown prior to coupling a handle sled to a handle base to form a handle unit;

FIGS. 5A-5C are perspective views of an exemplary handle unit of the vessel harvesting system of the present invention shown prior to and after coupling of the handle sled to the handle base, respectively;

FIGS. 6A-6B are alternative perspective views of a handle unit of the vessel harvesting system of the present invention shown, respectively, prior to and after coupling of the handle sled to the handle base;

FIGS. 7A-7D are cutaway and perspective views of one exemplary coupling feature between the handle sled and handle base;

FIGS. 11A-11E are enlarged views of an alternative handle unit of a vessel harvesting system, in which a severing/securing tool is mounted on a carriage that slides on a handle sled;

FIGS. 16A-16B are perspective views of one exemplary embodiment of a severing/securing tool actuation mechanism;

FIGS. 18A-18F are schematic views of alternative severing/securing tool rotation mechanisms;

FIG. 19 is a perspective exploded view of an exemplary mechanism for limiting rotation of the severing/securing tool shaft within the system; and FIGS. 19A-19H are alternative embodiments of cam washers for use in the mechanism of FIG. 19.

DESCRIPTION OF THE PREFERRED EMBODIMENTS

The present invention provides a vessel harvesting system that is easy to use and includes various subassemblies that are integrated for convenient and user-friendly operation. The vessel harvesting system is especially useful in minimally invasive endoscopic harvesting of blood vessels, including harvesting of the vessels of the extremities along the radial artery in the arm for use in coronary artery bypass grafting, and the saphenous vein in the leg for use in both coronary artery bypass grafting and peripheral artery bypass. Harvesting of other vessels, for example IMA, is also contemplated by the devices and methods of the present invention. In addition, the system is useful for dissection of ducts and other structures in the extraperitonial or subcutaneous extremity and thoracic space; the latter including exposure and dissection of structures external to the parietal pleura, including nerves, blood vessels and other tissues of the chest wall. It should be understood that the vessel harvesting system might also have use in a variety of other minimally invasive applications.

Figure 1A:
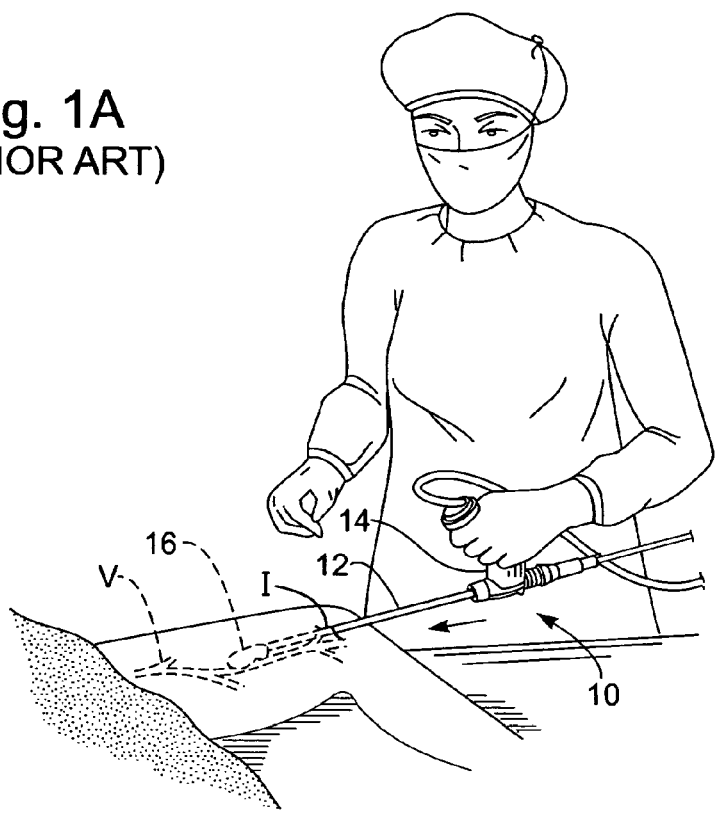
FIG. 1A is a schematic view of one step in a saphenous vein harvesting procedure of the prior art.
Figure 1B:
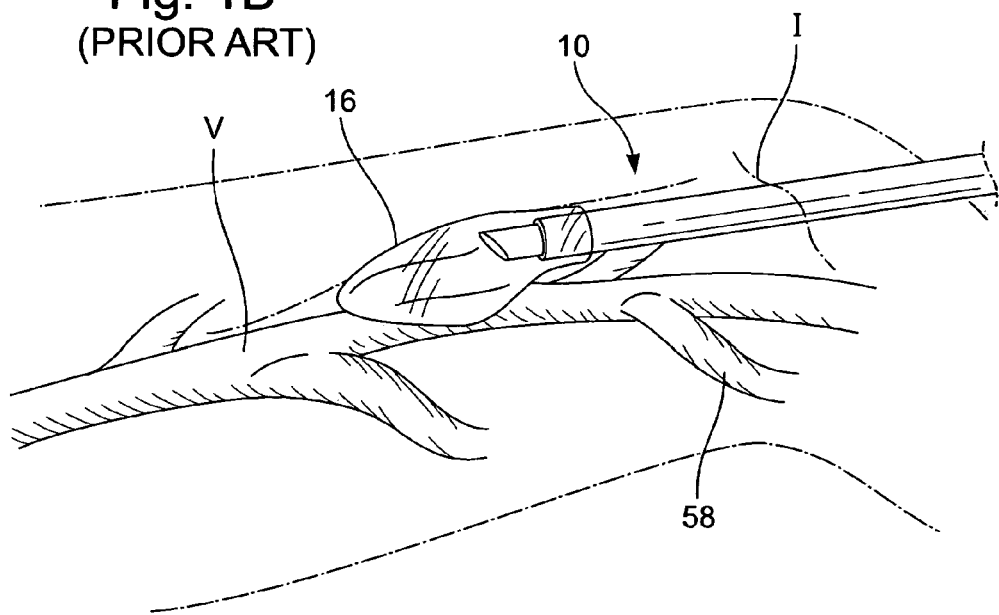
FIG. 1B is an enlarged view of a distal tip of the prior art vessel harvesting system of FIG. 1A in the process of dissecting tissue surrounding the saphenous vein.

One primary subassembly of the vessel harvesting system is a so-called "severing/securing tool" that is used to close off and separate side branches (i.e., side branches SB seen in FIG. 1B) from a primary vessel being harvested, and also possibly to sever the primary vessel. The term vessel severing/securing tool refers to any and all devices that accomplish a single function or any combination of the functions of severing, transecting, ligating, cauterizing, coagulating and/or sealing. For example, electrocautery tools such as bipolar scissors (or other plural electrode-based devices), monopolar devices, tissue bisectors (electrode loops), or thermally conductive tools such as tissue welders (hot wires) all provide these functions alone or in conjunction with an integral blade or cutter. Other devices which do not coagulate but instead ligate (i.e., tie off) or adhere the side branches may also be used.

Other similar devices using various acceptable sources of energy for sealing the tissue (for example, RF, microwave, laser, ultrasound, direct thermal energy, etc.) are also within the scope of the present invention. The severing/securing tool could be a single tool or a combination of plurality of separate tools each having its own function useful in vessel harvesting. The term "end effector" is used herein to refer to the distal operational portion of the various vessel severing/securing tools that may be used. One particular device that may be used in the vessel harvesting system of the present invention for both severing and coagulating a vessel is sold as the bipolar scissors available from Gyrus Group PLC, Reading, United Kingdom.

In one preferred embodiment, if a vessel severing/securing tool that utilizes coagulation is chosen, the tool is energized by conventional bipolar outputs of electrosurgical generators. Although a generator is required for use of the system, it is typically not packaged and sold with the system. For particular tissue bisectors such as that illustrated, use of such generators should not exceed a threshold power (e.g., 30 W) in any mode, and the user should not apply continuous cautery energy but instead should apply energy intermittently.

As with all minimally invasive vessel harvesting systems, the present system is performed under endoscopic visualization. The particular endoscope used may be packaged and sold separately from the components of the vessel harvesting system itself. In a preferred embodiment, a 7 mm Extended Length Endoscope is used. The length of the endoscope shaft may be specifically designed to match with the length of the cannula 23, or an off-the-shelf scope could be used as long as its length is adequate to reach the end of the cannula. A number of endoscopes from various manufacturers are suitable, but the user should verify compatibility with the system of the present invention and ensure that electrical isolation and grounding of the instruments is not compromised.

The present invention provides a "modular" handle unit for a vessel harvesting system. In this sense, modular means that there are at least two parts to the system which may be connected together, and that one of the parts, the "module," may be interchanged with a similar part. In the specific context of the handle unit of the present invention, a common handle base and attached cannula is designed to receive several different handle sleds having different vessel severing/securing tools associated therewith. In this sense, the vessel harvesting system is "modular" because the several vessel sled modules can be interchanged to mate with a common handle base.

A desirable feature of the vessel harvesting system of the present invention is the ability to operate easily and conveniently at least the movement control mechanisms of various tools of the vessel harvesting system without substantial rearrangement and movement of the hands of the user. For example, it will be advantageous to provide the user with ability to reach such controls and manipulate the tools with a palm of one hand placed on the handle. In this sense, "one-handed operation" signifies that the tool controls may be operated with one hand, although it is understood that in practice the user may choose to use two hands for stability or other reason.

After a more detailed description of a preferred system shown in FIG. 2, the various controls will become clearer. The handle unit of the device is described as preferably rigid. The term "rigid" as used here does not require absolute rigidity but rather means that the handle unit is generally solid. However, although the main body of the handle unit may be "rigid", certain auxiliary non-rigid features such as insufflation and irrigation tubes, and some moving controls, may be technically part of the handle unit. As such, the term "rigid handle unit" refers to a generally unitary firm body that may be held with one hand of the user. Similarly, the use of term "rigid" with reference to the cannula or cannula connection to the handle generally simply means "solid" or "firm."

Exemplary Vessel Harvesting System

FIG. 2 illustrates in a laid-out fashion various components of an endoscopic vessel harvesting system 20 of the present invention. The main element of the system 20 is a vessel harvesting tool 22 having a distal elongated cannula 23 and, on its proximal end, an integrated, preferably rigid, handle unit 24. In a preferred embodiment, the cannula 23 comprises a tube of biocompatible material such as stainless steel connected rigidly to the handle unit 24. Other suitable biocompatible materials could be used. An endoscope 26 having an elongated scope shaft 28 and proximal eyepiece 30 is sized to extend through a continuous lumen of the harvesting tool 22. The endoscope 26 further includes a proximal light post 32 for connection to a source of illumination, and the typically stainless steel shaft 28 encloses appropriate optical and illumination components. As mentioned above, the endoscope 26 may be provided as part of the entire system 20, or may be sold separately by the same or a different manufacture. In one preferred embodiment of the present invention, a removable transparent dissection tip 34 couples to a distal end 36 of the endoscope shaft 28 and functions as a dissector to create a cavity or tunnel surrounding a target vessel to be harvested, as will be described below. The remaining parts of the system (that could be included in the kit or sold separately) include a an access port 40 (sometimes also called a "short port blunt tip trocar" and used to provide a port of access for insertion of endoscopic instruments into an incision site) having an attached insufflation tube and nozzle 42, a small (e.g., 5 cc) syringe 44, a large (e.g., 30 cc) syringe 46, and a pair of annular seals 48a, 48b for use with the access port 40.

As will become more apparent from the detailed description below, the exemplary handle unit 24 seen in FIG. 2 comprises a distal handle base 50 coupled to a proximal handle sled 52. The cannula 23 desirably rigidly attaches to the handle base 50. A vessel severing/securing tool 54 (the distal end of which is seen projecting from a distal end of the cannula 23) and actuating carriage 56 is associated with the handle sled 52. Because the handle sled 52 can be decoupled from the handle base 50, it is a modular component as described above. Consequently, different vessel severing/securing tools 54 associated with different sleds 52 may be utilized with the same handle base 50 and cannula 23.

The handle unit 24 also features an endoscope hood 60 on its proximal end shaped to receive the eyepiece 30 and light post 32 of the endoscope 26. In a preferred embodiment, the vessel severing/securing tool 54 utilizes electrosurgical coagulation, and has electrically attached to it a cable 61 and bipolar connector 62. A flexible tube and connector 64 fluidly communicates with an inner space within the cannula 23 to provide an avenue for distal insufflation of $CO_2$ gas, as will be described below. Finally, a flexible tube and connector 66 fluidly communicates with a distal flushing port within the harvesting tool 22 to provide an avenue for injection of saline or other inert liquid for washing the distal end 36 of the endoscope shaft 28.

Integrated Electrical Connection Assembly

As mentioned above, one preferred severing/securing tool 54 utilizes electrosurgical coagulation and has attached to it a cable 61 and bipolar connector 62. Advantageously, as seen isolated in FIG. 2A, the present invention incorporates a one-piece electrical connection assembly 70 with integrated strain relief and wire interconnect. The electrical connection assembly 70 includes the pigtail connector cable 61, a strain relief grommet 72, a wire interconnect 73 and severing/securing tool lead wires 74 joined in parallel configuration. The pigtail connector cable 61 may consist of high strand count, rope overlay conductor with a pressure extruded Santoprene jacket to increase insulation adhesion, allowing for use of the strain relief grommet 72. The grommet 72 is, for example, Santoprene overmolded onto the pigtail cable 61, thus bonding securely with the jacket of the pigtail connector cable 61. The grommet 72 includes an intermediate channel that cooperates with rigid walls of the handle unit 24 to provide strain relief to the pigtail connector 61. The wire interconnect 73 provides an electrical junction between the pigtail connector 61 and the tool wire leads 74, and is protected by an overmolded Santoprene block. A service loop 76 comprises a portion of the tool lead wires 74 joined in parallel configuration by flexible heat shrink, thus allowing for high mobility of the severing/securing tool 54 with respect to the handle unit 24. The tool lead wires 74 may consist of high strand count Tefzel insulated wires that provide flexibility and abrasion resistance to facilitate routing through the handle unit 24.

The one-piece electrical connection assembly 70 simplifies manufacture of the vessel harvesting tool 22, and reduces part count, welding steps, and labor associated with current electrical assemblies. The assembly 70 provides an integrated, effective strain relief of the cable exiting the vessel harvesting tool 22 that is custom fit to simply slip into the tool, eliminating manufacturing and electrical arcing issues associated with tying a knot in the cable or other "add-on" methods of strain relief The integrated interconnect assembly 70 provides an electrically sound termination of the external power cable (pigtail 61) to the internal tool wires 74 of a different size and type, while protecting the junction with the interconnect block 73 and providing for easy capture and assembly along with the vessel harvesting tool 22. The high flex tool wires 74 and service loop 76 allow for easy routing through complicated internal paths of the handle unit 24. This also provides for high mobility for the severing/securing tool 54. Of course, the strain relief grommet 72 and interconnect 73 can be scaled up or down in size for different applications, and the wire types can be change to meet specific requirements of particular electrosurgical devices.

Exemplary Vessel Harvesting Technique

Prior to a more detailed explanation of the exemplary and alternative components of the vessel harvesting system 20, a preview of the use of the system is important for a preliminary understanding of the system functions.

FIGS. 3A-3D illustrate several discrete steps in a vessel harvesting procedure utilizing the system 20 seen in FIG. 2. The great saphenous vein is the longest vein in the body, extending from the foot and ending in the femoral vein just below the iliac veins and inferior vena cava. The saphenous vein ascends along the medial side of the leg in relation with the saphenous nerve. The portion typically harvested for use in CABG surgery extends upward from just above the knee toward the inner thigh area. To reiterate, simply for convenience and as an example, the description of the Figures is made with the reference to the saphenous vein, however, it is understood that a similar procedure may be utilized to harvest the radial artery or other suitable vessels, and the invention should not be construed as being limited to any particular vessel.

Figure 3A:
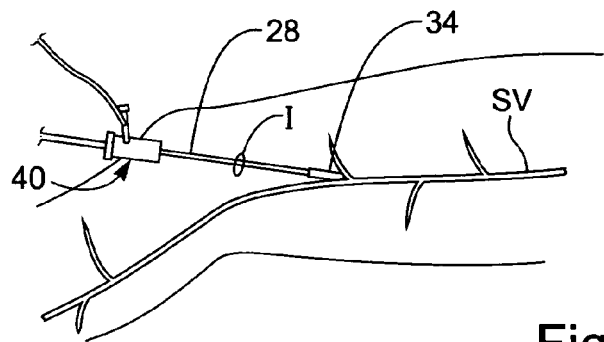
FIGS. 3A-3D are schematic views of several exemplary steps in a vessel harvesting procedure using the vessel harvesting system of the present invention.

FIG. 3A illustrates the insertion of the shaft 28 of the endoscope through an incision I such that the transparent dissection tip 34 is placed in the subcutaneous space anterior to the saphenous vein SV. The endoscope shaft 28 has previously been threaded through a 7 mm endoscope seal 48a (FIG. 2) mounted on the access port 40. The dissection tip 34 is then advanced along the vein SV until 3-4 cm of vessel is dissected from the surrounding tissue.

Figure 3B:
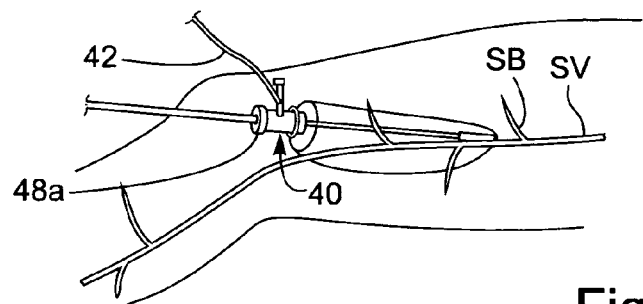

FIG. 3B shows the insertion of a main body of the access port 40 in the incision I. As is well-known in the art, the access port 40 may include in some embodiments a small balloon (not shown) around its main body that may be inflated to provide a sufficient gas seal against the incision I. A gas line connected to the insufflation tube and nozzle 42 supplies $CO_2$ gas under low-pressure to insufflate the dissected tunnel, thus opening it for improved visualization. The endoscope shaft 28 and dissection tip 34 are then advanced along the anterior aspect of the saphenous vein SV until the desired vessel length is dissected. Progress of the dissection is monitored via the endoscope 26. The endoscope shaft 28 and dissection tip 34 then may be withdrawn to the beginning of the tunnel and then advanced along the posterior aspect of the saphenous vein SV. The dissection continues gently and thoroughly, skirting vessel side branches SB as they are encountered. Upon completion of the dissection, the endoscope shaft 28 and dissection tip 34 may be removed, and the dissection tip could be disposed of.

Figure 3C:
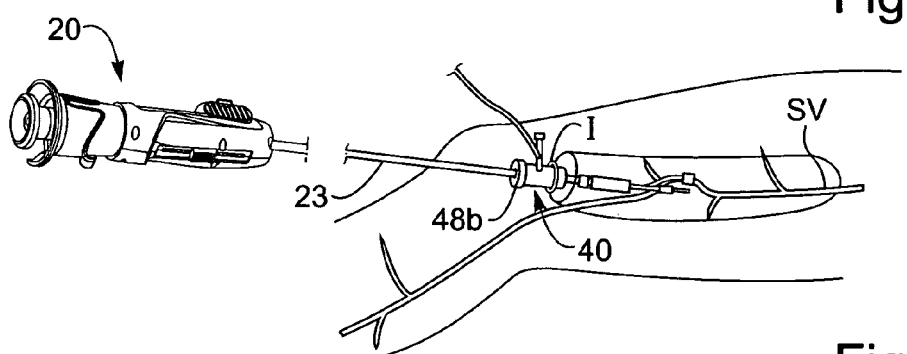
Figure 3D:
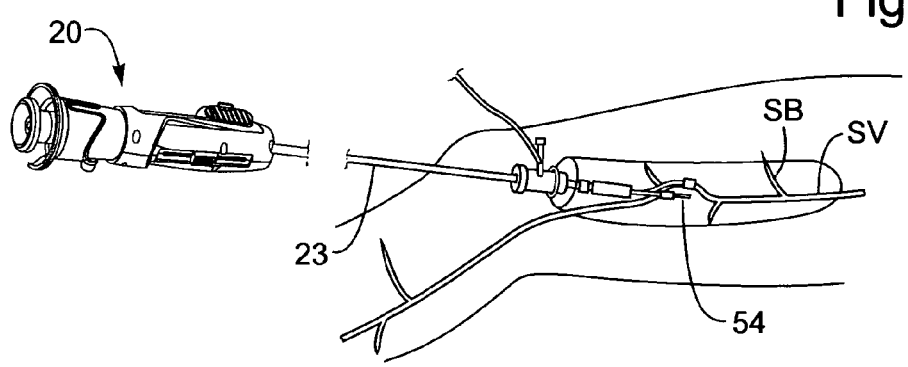

FIGS. 3C and 3D illustrate use of the harvesting system 20 of the present invention to retract, secure, and sever tributaries or side branches SB from the saphenous vein SV. With reference back to the system components of FIG. 2, a larger orifice cannula seal 48b is fitted to the access port 40. The endoscope 26 without the dissection tip 34 is then inserted through a continuous bore in the vessel harvesting tool 22. That is, the endoscope shaft 28 extends through the handle unit 24 and cannula 23. The entire assembly having the cannula 23 as the outer shaft member then inserts through the seal 48b of the blunt trocar tip 40. The trocar tip 40 is once again positioned and inflated at the incision I.

The gas line may again supply $CO_2$ to the insufflation tube and nozzle 42 (proximal insufflation). Alternatively, the gas line may be connected to the flexible tube and connector 64 to provide distal insufflation of gas through the cannula 23 to the cavity or tunnel. An infusion flow rate of 3-5 lpm to a pressure of 10-12 mmHg is adequate to hold the dissected tunnel open for improved visualization. Details of structure within the cannula 23 to ensure adequate distal gas outflow and prevent bubbles will be described below.

At this point, a specific discussion of use of the internal components of the vessel harvesting tool 22 will be postponed until those components are more explicitly shown and described. It is sufficient for the reader to understand at this stage that the system 20 comprising the vessel harvesting tool 22 and endoscope 26 functions to separate the saphenous vein SV from the surrounding tissue and side branches SB, at which point the vein is transected at one or both ends and removed or redirected for use for example, in the CABG surgery or other procedure requiring re-use of the vessel.

Exemplary Modular Vessel Harvesting Tool

FIGS. 4-6 are various exploded and assembled detailed views of a portion of the vessel harvesting system 20, primarily illustrating different views of the vessel harvesting tool 22, and in particular the handle unit 24.

Figure 4B:
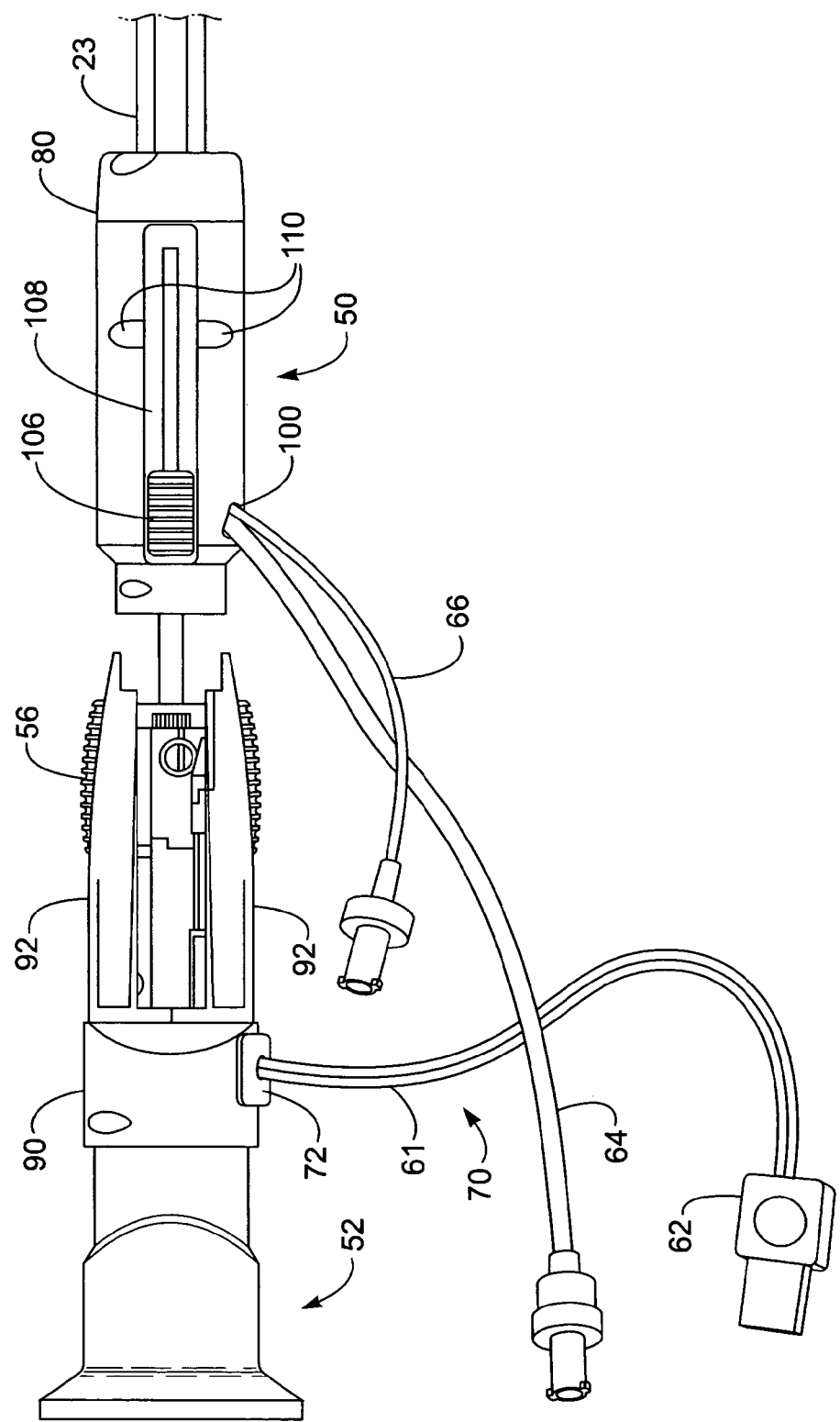

FIGS. 4A-4C show the exemplary handle unit 24 with the handle base 50 decoupled from the handle sled 52. The handle base 50 comprises a generally semi-cylindrical housing 80 having a distal ring-shaped flange 82 and a proximal landing 84 with ledges and cutouts designed to mate with features provided on the handle sled 52. The handle sled 52 has a proximal ring-shaped flange 90 against which the endoscope hood 60 abuts and a pair of distally projecting prongs 92. As seen in FIG. 4A, rails provided on the prongs 92 support the harvesting tool carriage 56 and enable proximal-distal displacement of the carriage with respect to the sled 52. FIG. 4B illustrates the underside of the prongs 92, and certain features provided thereon for mating with the landing 84 of the handle base 50, which will be detailed below with respect to FIGS. 7 and 8.

With specific reference to FIG. 4B, one exemplary integration of the electrical connector assembly 70 with the handle sled 52 is shown. Specifically, the over-molded strain relief grommet 72 is shown captured in an aperture formed in the proximal ring-shaped flange 90 of the handle sled 52 such that the pigtail cable 61 and bipolar connector 62 extend away from the handle sled 52. Although not shown, the wire interconnect 73 and lead wires 74 threaded through hollow spaces in one of the prongs 92 and are electrically connected with the severing/securing tool at the carriage 56. It will thus now be clear that the service loop 76 in the lead wires 74 provides some slack within the hollow prongs 92 such that the carriage 56 may be displaced along the sled 52 without tensioning and thus damaging the lead wires.

The underside of the handle base 50 shown in FIG. 4B also reveals an opening 100 therein through which the distal insufflation tube and connector 64 and irrigation tube and connector 66 enter the hollow housing 80. These tubes 64, 66 ultimately communicate with separate passages provided within the cannula 23, as will be explained below.

Figure 4D:
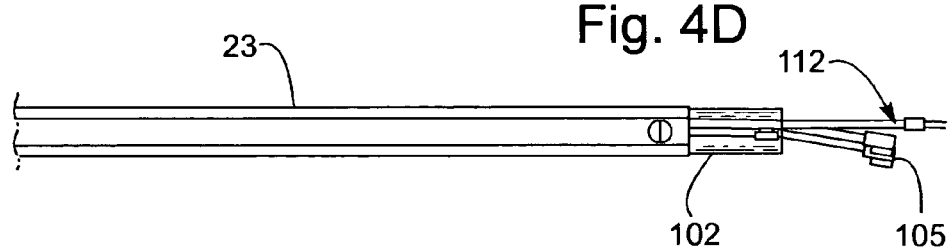
Figure 4E:
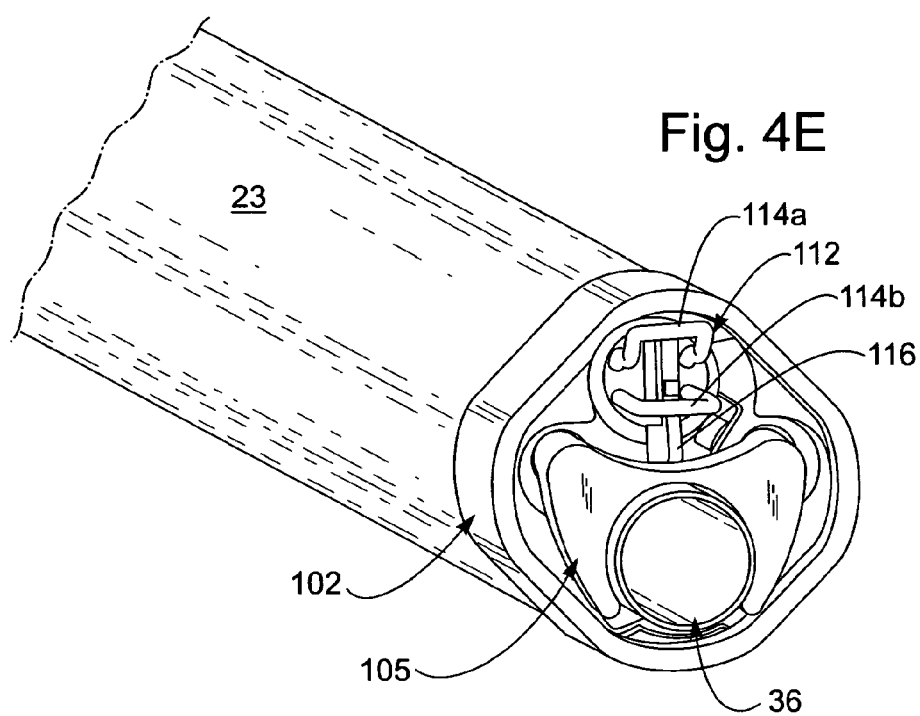

FIG. 4D illustrates a distal section of the cannula 23 which terminates in a blunt tip 102. The distal tip of a vessel cradle tool 104 (FIG. 4A) has a cradle ring 105 defining a generally C-shaped opening therein for capturing and holding the vessel being harvested. The cradle ring 105 may project from the blunt tip 102 as shown, though it can also be retracted within the tip as seen in FIG. 4E. The vessel cradle tool includes at least one actuating rod that extends proximally the length of the cannula 23 to the handle base 50 and is displaced in a proximal-distal direction, for example, by a slider 106 captured in a linear slot 108 of the housing 80, as seen in FIG. 4B.

The slider 106 in FIG. 4B is shown in its retracted position within the slot 108 corresponding to retraction of the cradle ring 105 within the cannula 23 into the position shown in FIG. 4E. The present invention also provides a feature on the handle base 50 that easily and reliably notifies a user of the relative proximal-distal position of the vein cradle tool. Namely, FIG. 4B illustrates a pair of rounded tactile feedback bumps 110 formed in the housing 80 on either side of the guide slot 108 that contact the user's thumb as it displaces the slider 106. The user may repeatedly position the slider 106 relative to the bumps 110 without looking down at the handle unit 24 because of a tactile feedback provided by the bumps 110. The significance of the location of the bumps 110 will be explained below after a better understanding of the interaction of the vessel cradle tool with the severing/securing tool 54.

As mentioned above, the severing/securing tool 54 may take the form of a variety of devices for both severing and securing or closing off vessels, typically tributaries of a main vessel being harvested. In the exemplary embodiment, the severing/securing tool 54 is a bipolar tissue bisector that includes electrodes for coagulating tissue and a sharp blade for severing. A distal end effector 112 of the severing/securing tool 54 is seen in FIG. 4E, and in the various side views of FIGS. 4A, 4B and 4D. In the embodiment of FIG. 4E, the end effector 112 includes a pair of coagulation electrodes 114a, 114b and a pivoting blade 116. In the orientation shown, a vessel is placed horizontally between the generally U-shaped electrodes 114a, 114b and energy applied thereto to coagulating tissue in two places. After coagulation, the blade 116 pivots through the U-shaped openings in the electrodes 114 and severs the vessel between the points of coagulation.

Figure 4F:
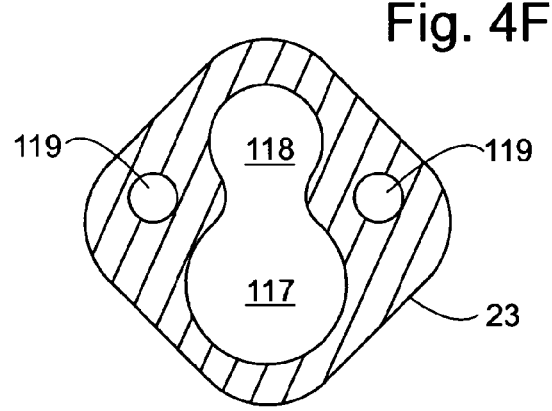

An exemplary cross-section of the tube of the cannula 23 is seen in FIG. 4F. A plurality of passages or lumens extend the length of the cannula 23 from the handle unit 24 to the blunt tip 102. These lumens provide space for the various harvesting tools, as described herein, and also permit distal insufflation of gas through the cannula 23, and around the tools. The lumens may be separate, or some or all of them may be in fluid communication. In other words, the word lumen as used herein does not necessarily imply a complete divider. For example, the illustrated embodiment shows a large, generally figure-8 shaped lumen having a generally cylindrical first section or lumen 117 separated from a somewhat smaller cylindrically-shaped second section or lumen 118 by a narrowing of the cannula body therebetween. A pair of separate smaller lumens 119 extend through the cannula 23 on either side of the figure-8 shaped lumen. The blunt tip 102 as seen in FIG. 4E has similar apertures such that the first lumen 117 is sized to receive a 7 mm endoscope 36, the second lumen 118 is sized to receive the end effector 112 of the severing/securing tool, and the two smaller lumens 119 each receive rods provided for axially displacing the cradle tool 105. It should be understood that other arrangements of lumens, separate or otherwise, are contemplated within the cannula 23.

In each of FIGS. 4A-4C the handle base 50 is shown spaced from and not coupled to the handle sled 52 (so that it is easier to describe and explain the constructions of the device), and thus the severing/securing tool 54 is not fully extended (however, the end effector 112 is visible through the blunt tip 102). The end effector 112 is shown in FIG. 4D fully extended and projecting past the blunt tip 102. To attain this position, the handle unit 24 is formed by coupling together the handle base 50 and handle sled 52, and the tool carriage 56 is displaced in a distal direction with respect to the handle sled prongs 92, as seen in FIG. 5B.

FIG. 4D illustrates the vessel cradle ring 105 in a proximal position with respect to the end effector 112. This position corresponds to the position of the slider 106 in FIG. 4B, that is, proximal to the raised tactile feedback bumps 110. Desirably, to position the cradle ring 105 at the same location as the end effector 112 (when the end effector is fully extended), the slider 106 must be positioned at the tactile feedback bumps 110. Finally, to position the cradle ring 105 distally with respect to the end effector 112, the slider 106 must be positioned distally past the raised bumps 110. It should be noted that the user may not desire that the cradle ring 105 be at the same location as the end effector 112 during the procedure, the tactile feedback bumps 110 merely providing information as to the relative position of the two elements. These relative positions of the vessel cradle ring 105 and severing/securing tool end effector 112 are alternately utilized during the vessel harvesting procedure. The provision of the tactile feedback bumps 110 on the handle unit instantly informs the user of the locations of these tools. Therefore, in conjunction with the visual image provided by the endoscope 26, the tactile feedback bumps 110 help speed up the entire procedure.

Furthermore, the tactile feedback bumps 110 may also be used to rapidly clear an occluded endoscope lens. As disclosed in U.S. Pat. Nos. 6,176,825 and 6,406,425, the irrigation tube 66 (FIG. 4B) may be in fluid communication with an endoscope flushing nozzle (not shown) associated with the vessel cradle ring 105. As the harvesting procedure progresses, the lens on the distal end 36 of the endoscope shaft may become occluded with tissue or blood. Extension of the vessel cradle tool positions the flushing nozzle a short distance in front of the endoscope lens at which point fluid infused through the tube 66 sprays backward and clears the lens. Positioning the slider 106 adjacent the tactile feedback bumps 110 may also indicate the proper extension of the vessel cradle tool to ensure optimum flushing of the endoscope lens, which operation can therefore be accomplished rapidly without visual inspection.

With reference now to FIGS. 5A-5C and 6A-6B, the control features for the severing/securing tool 54 will be described. As mentioned, the end effector 112 seen best in FIG. 4E enables transection and coagulation of specific target vessels, typically side branches off the main vessel. In addition, the end effector 112 is capable of rotation generally about the axis of the harvesting tool cannula 23 so that it may be properly positioned with respect to the target vessel. Finally, the end effector 112 can be retracted within the cannula 23, or axially extended in use as seen in FIG. 4D. Desirably, controls for three of these four functions (the movement controls) are integrated into the handle unit 24, and only the application of electrical energy is controlled elsewhere. Specifically, the bipolar generator electrically coupled to the bipolar connector 62 (FIG. 4B) typically has a foot switch or other such control to apply the electrical current. However, is entirely feasible that the coagulating current control switch could also be incorporated within the handle unit 24.

Some of the exemplary control mechanisms are described below. Axial displacement of the tool carriage 56 with respect to the handle sled 52 translates into identical axial movement of the end effector 112. The tool carriage 56 includes a serrated pad 120 on both sides which provides the user with a non-slip surface to displace the carriage 56. An elongated distal shaft 122 connects the tool carriage 56 to the end effector 112 and carries the appropriate control linkages. Without going into further detail, the control linkages include electrical wires to conduct the coagulation energy and at least one wire or rod to actuate the severing blade 116. Movement of the blade 116 occurs upon depression of a toggle switch 124 mounted within the carriage 56, which may push a rod or pull a wire, depending on the mechanics of the tool. Ideally, the blade 116 is preloaded into its retracted position, and depressing the toggle 124 pulls a wire to cause the blade to extend between the U-shaped electrodes 114a, 114b so as to be poised for severing a vessel. Finally, rotation of the distal shaft 122 about its axis occurs upon actuation of a serrated rotation wheel 126 mounted within the carriage 56. The specifics of the mechanism for rotating the shaft 122 will be described below.

FIG. 6B best illustrates the integrated nature of the movement controls of the severing/securing tool 54 within the handle unit 24. That is, the handle unit 24 presents as a generally rigid cylindrical handle that could be manipulable by one hand of the user. By holding the handle unit 24 with the right hand, the user can alternately place his or her thumb on the serrated pad 120, toggle switch 124, or rotation wheel 126. With one digit, therefore, the user can translate the end effector 112 axially, rotate the end effector about its axis, and actuate the severing blade 116. As mentioned above, application of the coagulating current is typically accomplished with a foot switch associated with the generator. Moreover, FIG. 5C illustrates the position of the slider 106 around the handle unit 24 which can be displaced by a finger on the right hand of the user. Gross linear and angular movement of the harvesting tool cannula 23 is of course accomplished by movement of the user's arm.

In a typical vessel harvesting procedure, the user locates a target side branch around the main vessel with the endoscope 26 and positions the blunt tip 102 in proximity therewith. The C-shaped cradle ring 105 extends to the targeted side branch by advancing the slider 106. One primary function of the cradle ring 105 is to provide optimal presentation of the side branch while maintaining space between the main vessel and the site at which the end effector 112 severs and coagulates. By displacing the tool carriage 56 on the handle unit 24 the end effector 112 advances to capture the side branch. The end effector 112 may be rotated by the rotation wheel 126 to orient the transection blade 116 perpendicular to the side branch. Depressing a distal end of the toggle switch 124 extends the severing blade 116 to its cutting position. The target side branch is positioned between electrodes 114a, 114b, and the electrocautery current is activated via the generator foot switch. Successful coagulation is observed through the endoscope 26 by the presence of tissue dehydration and blanching. After coagulation, the user releases the toggle switch 124, or depresses the opposite end thereof, causing the blade 116 to retract and transect the coagulating tissue.

For the most efficient harvesting procedure, at least one or both of the cradle ring 105 and end effector 112 rotates with respect to the other or with respect to the cannula, and provides a relative degree of freedom therebetween. In the exemplary method, the cradle ring 105 may be rotated by overall rotation of the harvesting tool cannula 23 to best grasp and secure the primary vessel, after which the end effector 112 rotates into its optimal position (e.g., perpendicular to the side branch). With the addition of an additional rotation mechanism, the reader will see that the cradle ring 105 may also be capable of rotation separately from the cannula 23. Alternatively, the cradle ring 105 may be able to rotate within the cannula 23, while the end effector 112 remains oriented in the same angular position and can only be displaced linearly. In the latter alternative configuration, the method may involve first rotating the cannula 23 such that the transection blade 116 is perpendicular to the side branch, after which the cradle ring 105 is rotated and extended to grasp the primary vessel. In its broadest sense, therefore, the present invention provides a rotation mechanism in the handle unit for at least one of the vessel cradle tool and severing/securing tool.

Modular Handle Unit Assembly

Figure 8A:
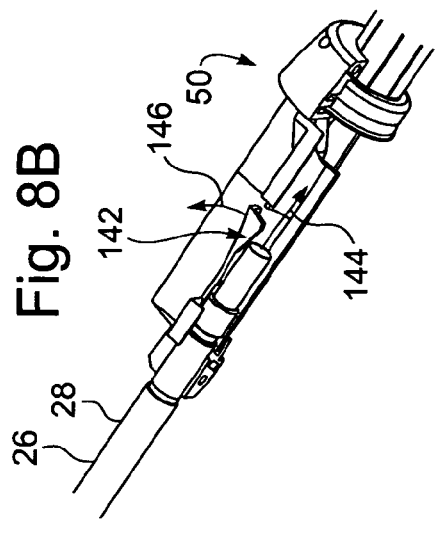
FIGS. 8A-8D are cutaway and perspective views of an exemplary locking feature between the handle sled and handle base initiated by introduction of an endoscope cannula through the handle unit.
Figure 8C:
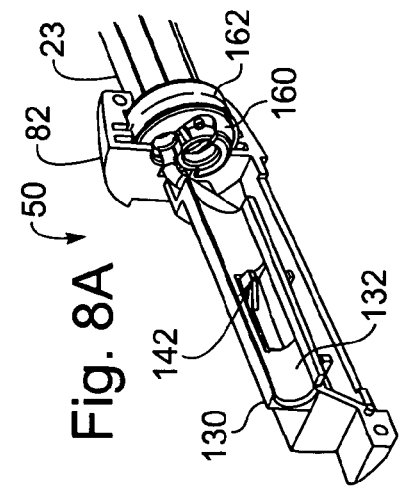

FIGS. 7A-7D illustrate in detail the aforementioned cooperation of the handle base 50 and the handle sled 52, and in particular one exemplary coupling feature therebetween that indicates to the user when the two components are fully seated, and thus when the handle unit 24 is assembled and ready for introduction of the endoscope 26. The proximal landing 84 on the handle base 50 includes a pair of raised walls 130 that have a generally rectangular parallelepiped shape and an internal cylindrical bore 132. The cylindrical bore 132 is sized to receive the endoscope shaft 28, as best seen in FIG. 8C. The distal ring-shaped flange 82 defines a circular opening 134 through which the severing/securing tool shaft 122 extends. As will be explained more fully below, the flange 82 houses an annular seal with appropriate apertures for passage of both the endoscope shaft 28 and tool shaft 122.

With specific reference to FIGS. 4B and 7A, the underside of the handle sled 52 is shaped to closely mate with the landing 84 of the handle base 50. That is, the dual prongs 92 are spaced apart approximately the same distance as are the walls 130 on the landing 84. Although not shown in FIGS. 7A and 7B, the severing/securing tool shaft 122 inserts through the circular opening 134 to align the handle base 50 and handle sled 52. FIG. 7A illustrates a small angular cutout 136 on one of the walls 130, while FIG. 7B shows a mating triangular tab 138 on one of the prongs 92 of the handle sled 52. When the handle sled 52 is moved in the direction of arrow 140 in FIG. 7C, the tab 138 deflects around the proximal end of the corresponding wall 130 and into the cutout 136, as seen in FIG. 7D. This detent operation produces an audible click or tactile snap that indicates to the user that the handle unit 24 is assembled. It should be noted that the wall 130 that includes the cutout 136 may deflect inward because at this stage the endoscope shaft 28 has not been introduced into the handle unit 24. The illustrated embodiment does not "lock" the base and sled together, but instead the two parts click together and can be separated by pulling the base and sled apart axially.

Those of skill in the art will understand that numerous such detent features could be substituted for those shown, as well as other locking/cooperation mechanisms for connecting handle base 50 and the handle sled 52 could be used, and the invention should not be construed as being limited to the illustrated embodiment. Indeed, the present invention also contemplates providing a more secure coupling structure which does "lock" the base and sled together. The particular lock may be configured to resist separation from the user simply pulling the base and sled apart axially, but would release upon application of a twist or push force, or by activating a release lever.

It is important to point out once again that the handle sled 52 and particular severing/securing tool associated therewith is a modular unit that can be replaced with a similar sled having a different tool. Therefore, the handle base 50 may couple with a handle sled having a tissue bisector, a handle sled having bipolar scissors, or a handle sled having a tissue welder or other tool useful in vessel harvesting, depending on user preference. Indeed, different tools have different strengths in various applications; for instance in harvesting the radial artery in the arm versus the saphenous vein in the leg. The handle base 50 attaches to the cannula 23 and incorporates vessel cradle and extension controls, distal insufflation tubing and passages, and a flushing system for the endoscope. With the addition of the handle sled 52, the fully assembled handle unit 24 has a complete integrated set of tools and controls for the harvesting procedure, and is constructed in a single or unitary handle configuration that is easy and convenient to operate. Moreover, as will be apparent below in conjunction with a description of FIGS. 15A-15C, a modified handle sled that accommodates a conventionally operated severing/securing tool may also couple with the handle base 50. In this sense, the modularity of the present invention should not be considered limited to forming an integrated or unitary handle unit.

Figure 8B:
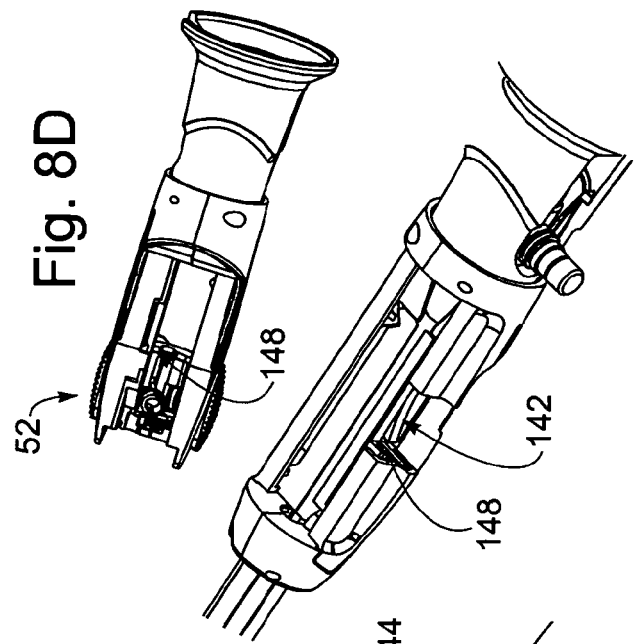
Figure 8D:
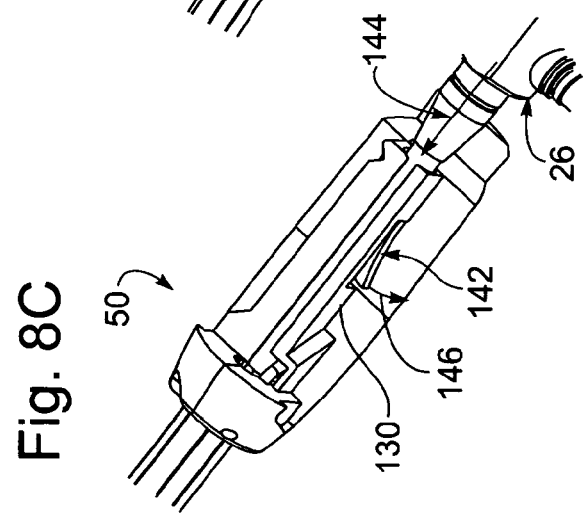

In some embodiments, subsequent to coupling the handle base 50 to the handle sled 52, the endoscope 26 is introduced to lock these two elements together (unless the base and sled are already "locked" together). FIGS. 8A-8D illustrate in cutaway form the locking mechanism within the handle unit actuated by introduction of the endoscope 26. In FIG. 8A, a cantilevered locking tab 142 is shown projecting into the bore 132 from one of the walls 130. As seen in FIG. 8B, introduction of the endoscope 26 in the direction of arrow 144 cams the locking tab 142 outward in the direction of arrow 146. FIG. 8C shows the same action from a different perspective to illustrate the final position of the locking tab 142 which ends up projecting outward from the associated wall 130. Finally, FIG. 8D illustrates a notch or cutout 148 on the underside of the handle sled 52 that receives the deflected locking tab 142. Because of the material interference between the locking tab 142 and proximal shoulder on the cutout 148, the handle base 50 and handle sled 52 are secured together. Furthermore, presence of the endoscope shaft 28 within the bore 132 helps to lock the aforementioned triangular tab 138 into the slot 136, which further secures the assembled handle unit 24.

Figure 9A:
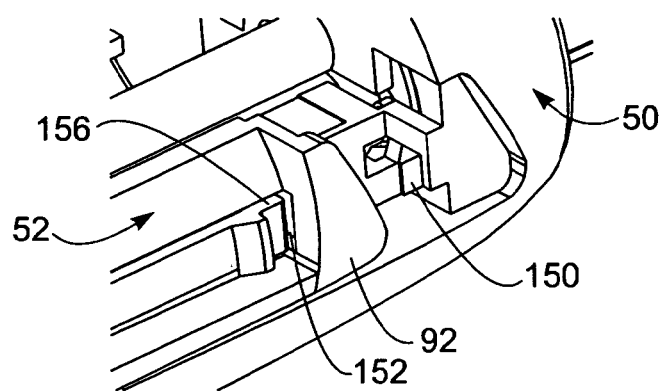
FIGS. 9A-9B are partial perspective views of an optional carriage locking feature of the present invention.
Figure 9B:
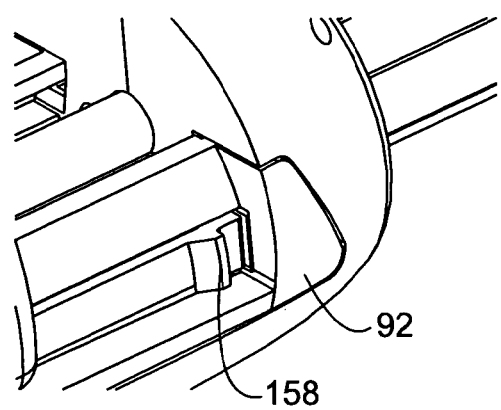

FIGS. 9A and 9B illustrate an optional feature of the present invention that locks the position of the severing/securing tool 54 on the handle sled 52 prior to assembly of the handle unit 24. This feature is not illustrated in the exemplary embodiment of FIGS. 2-8, although it could be easily incorporated therein. FIG. 9A shows a small triangular pawl 150 molded into the handle base 50 and extending in a proximal direction from the disk-shaped flange 82. One of the prongs 92 of the handle sled 52 is shown just prior to fully coupling the sled to the base. The tool carriage 56 is seen in phantom for clarity. A forward or distal end of the prong 92 includes an aperture for receiving the pawl 150. Once the base 50 and sled 52 are fully coupled, as seen in FIG. 9B, the pawl 150 projects through the aperture 152 and engages a cam surface 154. Displacement of the cam surface 154 disengages a latch 156 on the tool carriage 56. The latch 156 is initially spring-loaded to engage a small block 158 on the prong 92 and hold the tool carriage 56 in place on the handle sled 52. Once the handle base 50 and handle sled 52 are fully assembled, the pawl 152 remains in place to prevent re-engagement of the latch 156 and block 158, therefore freeing the tool carriage 56 for sliding movement along the handle sled.

Because the tool carriage 56 is initially held at the distal end of the sled 52, the task of inserting the tool shaft 122 through the handle base 50 and cannula 23 is made easier because the tool shaft remains fixed with respect to the handle sled. Furthermore, positioning the tool carriage 56 at the distal end of the prongs 92 adds rigidity thereto and further facilitates assembly of the handle unit 24.

Distal Insufflation

As previously mentioned, it may be desirable to advance the vessel harvesting procedure with $CO_2$ insufflation to provide adequate space around the vessel being harvested for visualization and to ensure minimal trauma to the vessel and surrounding tissue during the procedure. Some harvesting systems make use of a proximal insufflation port at the site of incision, such as through the access port 40 as seen in FIGS. 3A and 3B. It has been discovered that insufflation of $CO_2$ gas within the cavity can be improved by replacing or supplementing the proximal infusion of gas with a distal infusion, specifically from the distal end of the cannula 23. In its broadest sense, therefore, the present invention provides gas passages extending from the distal insufflation tubing and connector 64 seen in FIG. 2 to the distal end of the cannula 23.

Figure 10A:
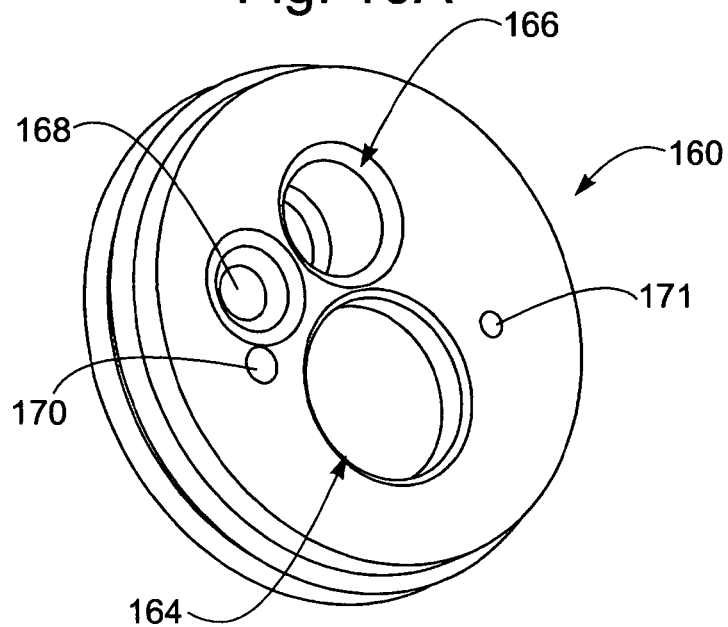
FIGS. 10A-10B are front and rear perspective views of an exemplary main cannula seal of the vessel harvesting system of the present invention.
Figure 10B:
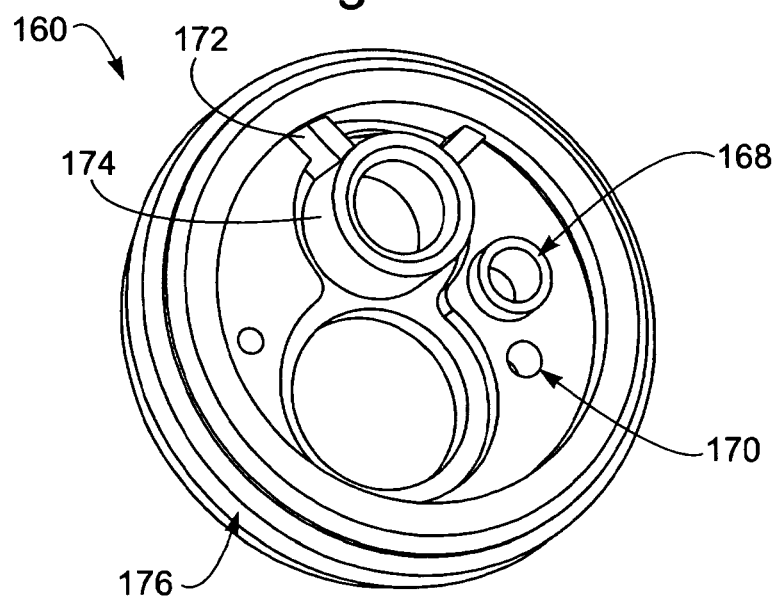

To ensure proper application of the distal gas insufflation, and in particular to maintain adequate pressures within the cavity, a gas seal 160 seen in FIGS. 10A and 10B is provided at the distal end of the handle unit 24 through which the various harvesting tools pass. FIG. 8A best illustrates placement of the seal 160 at the distal end of the handle base 50. Specifically, the seal 160 fits closely within an enlarged cross-section proximal shoulder 162 on the harvesting tool cannula 23, which in turn is captured within the molded disk-shaped flange 82 of the handle base 50. FIG. 10C-10G illustrate in perspective several alternative embodiments of the tool cannula 23, and the multi-faceted embodiment of FIG. 10D is closest to that illustrated in FIG. 8A.

FIG. 10A illustrates a front or proximal face of the seal 160, while FIG. 10B shows the rear or distal face. The seal 160 includes an endoscope orifice 164, a severing/securing tool orifice 166, a distal insufflation orifice 168, a scope wash tube orifice 170, and a tool cradle wire orifice 171. Each of the first three of these orifices includes a lead-in chamfer, as seen in FIG. 10A to facilitate introduction of the respective shafts. The rear face of the seal 160 includes a plurality of gussets 172 and reinforcing walls 174 surrounding the orifices. A peripheral flange 176 maintains the circular integrity of the seal 160 and closely fits within an inner surface of the proximal shoulder 162 on the harvesting tool cannula 23. The seal 160 may be made of an elastomeric material such as silicone so that the orifices can be slightly undersized with respect to the shaft being received and therefore provide a tight seal thereagainst. The gussets 172 and reinforcing walls 174 help prevent inversion of the seal when the endoscope shaft 28 or tool shaft 122 are extracted from the handle base 50.

In its simplest form, the distal insufflation subsystem includes the flexible tube and connector 64 seen in FIG. 2, with the tube extending through the hollow housing 80 of the handle base 50 into sealing engagement with the distal insufflation orifice 168. The orifice 168 extends completely through the seal 160 and into fluid communication with an internal passage within the cannula 23. Infusion of gas through the tubing 64 therefore introduces gas to the interior of the cannula 23, to ultimately egress from a distal end thereof.

Figure 10C:
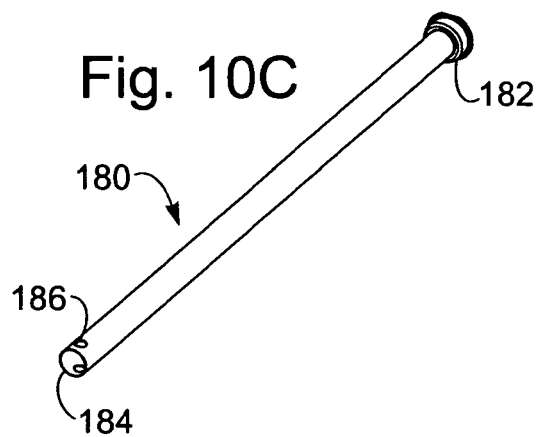
FIGS. 10C-10G are perspective views of an exemplary main cannula and several alternative internal gas insufflation cannulas/diffusers that cooperate with the seal of FIGS. 10A-10B to deliver gas to a distal end of the vessel harvesting system.
Figure 10D:
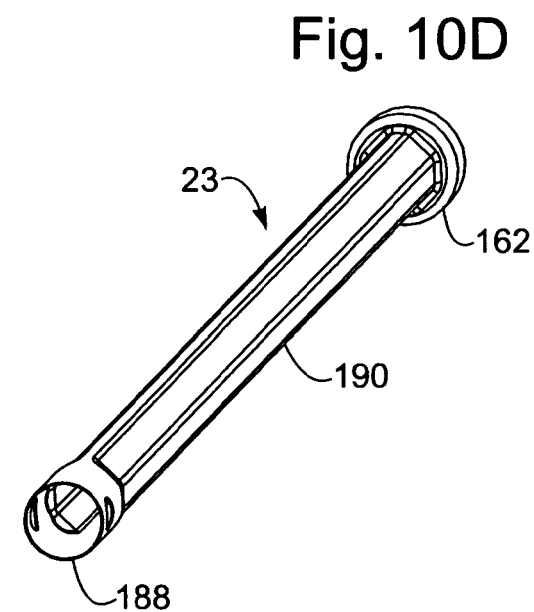

FIG. 10C illustrates a simple solid tubular cannula 180 including an enlarged proximal shoulder 182. In this embodiment, gas passes from the proximal end at the shoulder 182 to a distal end 184 around the endoscope and harvesting tools extending through the cannula 180. A small orifice 186 seen at the distal end 184 may be used to secure a blunt tip to the cannula, such as blunt tip 102 of FIG. 4E.

FIG. 10D illustrates an exemplary embodiment of the cannula 23 extending from the enlarged cross-section proximal shoulder 162 to a distal end 188. A midsection 190 of the cannula 23 has a non-circular configuration, and in particular includes elongated facets so as to have a polygonal tubular shape. Possible noncircular cross-sections include hexagonal, octagonal, and other irregular patterns. A non-circular cross-section may provide better gas insufflation because gas which egresses from the distal end 188 (or through a blunt tip 102) better seeps in a proximal direction around the cannula 23 the length of the tissue cavity. One potential reason for enhanced insufflation is that tissue may not attach to the faceted surface of the cannula 23 as well as it does to a tubular cannula surface. Indeed, laboratory tests have verified that the quality of insufflation is enhanced with a non-circular cannula 23.

Certain non-circular cross-sections may be designed to custom fit the internal tool layout along the length of the cannula. Another benefit to the faceted midsection 190 is the ability to enhance blunt dissection by rotating the cannula 23 about its axis. Furthermore, non-circular cross- sections may be designed to have better hoop and longitudinal strengths than a simple tubular shape. The cannula 23 may be manufactured using various methods, including hydroforming, extrusion, or protrusion, and may be made of suitable metal (e.g., stainless steel) or plastic (e.g., Delrin).

Figure 10E:
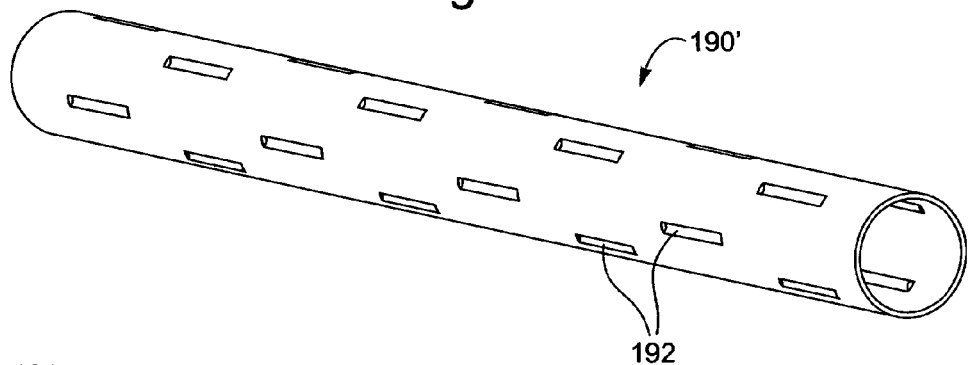
Figure 10F:
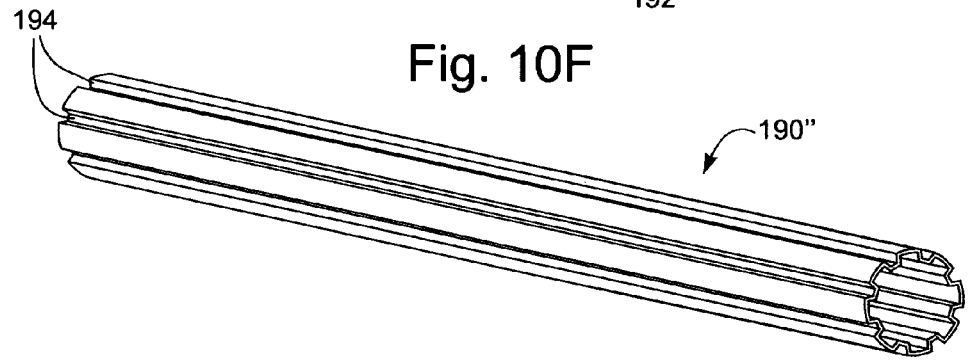

FIGS. 10E-10F are further alternative designs for the midsection 190 of the cannula 23 that enhance gas flow insufflation. In the midsection 190' of FIG. 10E, the otherwise tubular cannula includes a plurality of circumferential rows of discontinuous recesses or channels 192. These channels 192 provide interruptions to constrictions caused by surrounding tissue pressing against the surface of the cannula. The interrupted channels 192 allow gas to migrate down the length of the tunnel. The circumferentially offset rows of channels 192 may also be arranged in spiral, staggered, or other patterns. The midsection 190" shown in FIG. 10F includes a plurality of axially-oriented continuous channels 194 that also help ensure adequate flow of gas from one end of the cannula to the other.

Figure 10G:
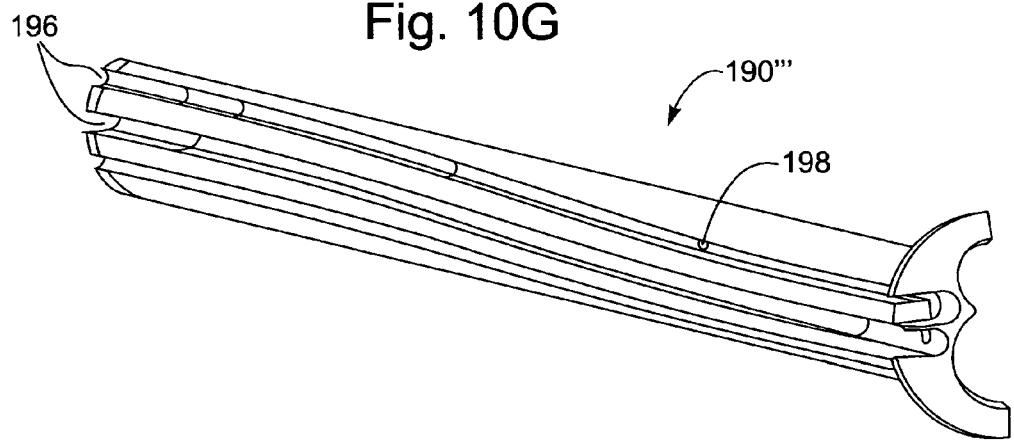

Finally, FIG. 10G illustrates a midsection 190''' of a plastic insert that fits within any of the aforementioned cannulas and includes elongated channels 196 extending its length that are arranged in slight spirals. Moreover, small cross-section holes 198 extend between the channels to allow cross flow of gases. Multiple channels allow for flow to be redirected through another channel in the event one or more becomes clogged. Furthermore, the distributed flow of gas through the channels 196 helps prevent bubbles from forming at a single flow point.

Alternative Modular Handle Units

FIGS. 11-15 illustrate various alternatives of modular vessel harvesting handle units of the present invention. All but the embodiment shown in FIGS. 15A-15C are integrated, meaning at least the movement controls for the various vessel harvesting tools are provided on an integral handle (as was previously explained, certain controls, for example, a foot pedal for energy supply activation may not be located on the handle).

FIGS. 11A-11E are various perspective views of a handle unit 200 of a vessel harvesting tool comprising a handle sled 202 that couples to a handle base 204. The handle unit 200 is substantially similar to the earlier described handle unit 24, and includes a severing/securing tool carriage 206 mounted for axial movement along the handle sled 202. Again, the particular kind of severing/securing tool may be selected by the user such that different handle sleds 202 having different tools can mate with a common handle base 204.

In the embodiment of FIGS. 11A-11E, the handle sled 202 includes a pair of rails 208 that terminate at a distal end in an abutment wall 210 constraining the tool carriage 206 from separating from the handle sled. The construction of the mating surfaces between the handle sled 202 and handle base 204 are also somewhat different than the earlier-described embodiment.

FIGS. 12A-12D illustrate a vessel harvesting system 220 having an endoscope 222 that works in conjunction with a vessel harvesting tool 224. The vessel harvesting tool 224 includes a tool cannula 226 extending distally from a handle base 228, and a severing/securing tool comprising an elongated shaft 230 extending distally from a tool carriage 232 and terminating at an end effector 234. The harvesting tool 224 further includes an endoscope-receiving hood 236 that couples to a proximal end of the handle base 228 but is shown exploded therefrom in FIG. 12A.

Figure 12A:
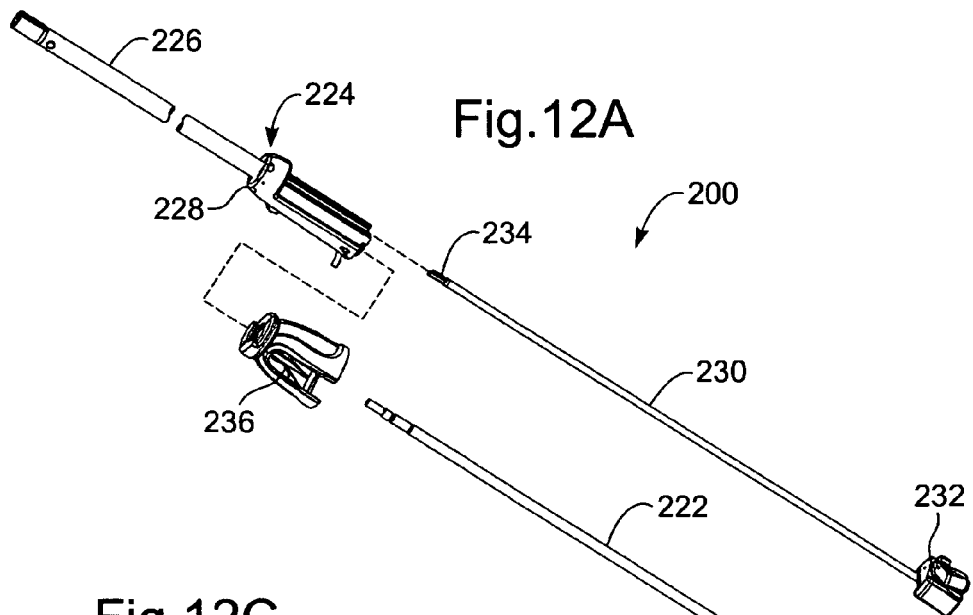
FIGS. 12A-12D are perspective exploded views of an alternative vessel harvesting system of the present invention.
Figure 12C:
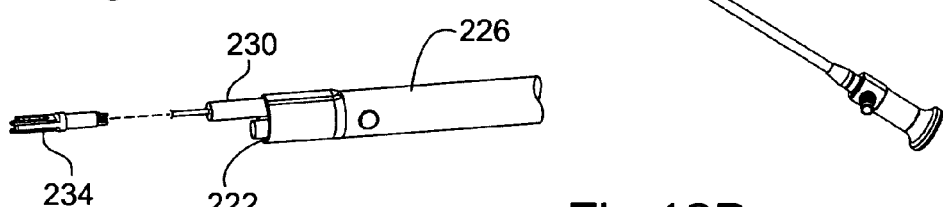
Figure 12B:
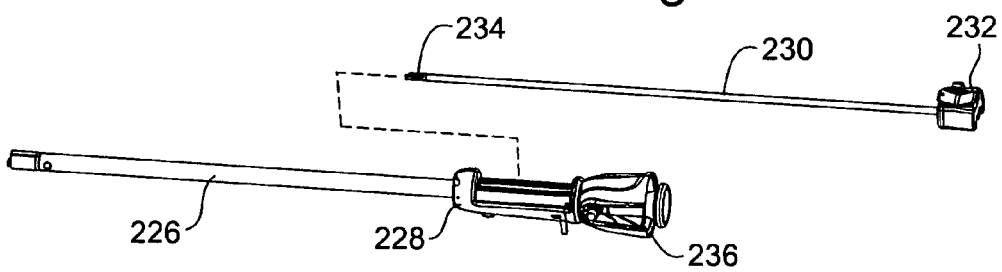
Figure 12D:
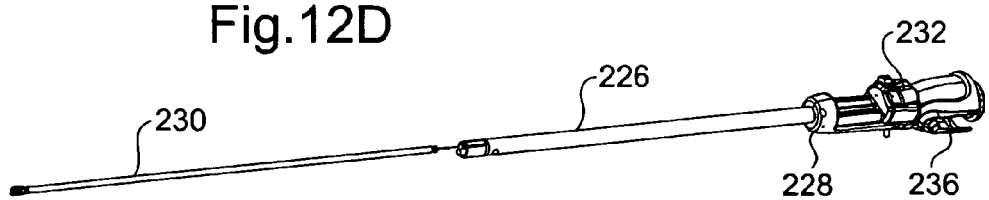

The main difference in the embodiment of FIGS. 12A-12D from the earlier described system 20 is that the integrated handle seen in FIG. 12D does not comprise an assembled handle base and handle sled. Instead, the severing/securing tool carriage 232 is arranged to couple and slide with respect to longitudinal rails provided on the handle base 228. The endoscope-receiving hood 236 snaps onto a proximal end of the handle base 228, and acts as an end cap to retain the severing/securing tool carriage 232 in place. The assembled vessel harvesting tool 224, handle base 228, and endoscope-receiving hood 236 form a unitary handle unit that has the controls of the tool incorporated thereon, -and functions in the same manner as the system 20 described above. It will be understood that the embodiment of FIGS. 12A-12D is also modular in that the severing/securing tool carriage 232 is removable. The endoscope-receiving hood 236 may be detached or displaced out of the way, and a different severing/securing tool and carriage can be coupled to the rails of the handle unit 228.

Figure 13A:
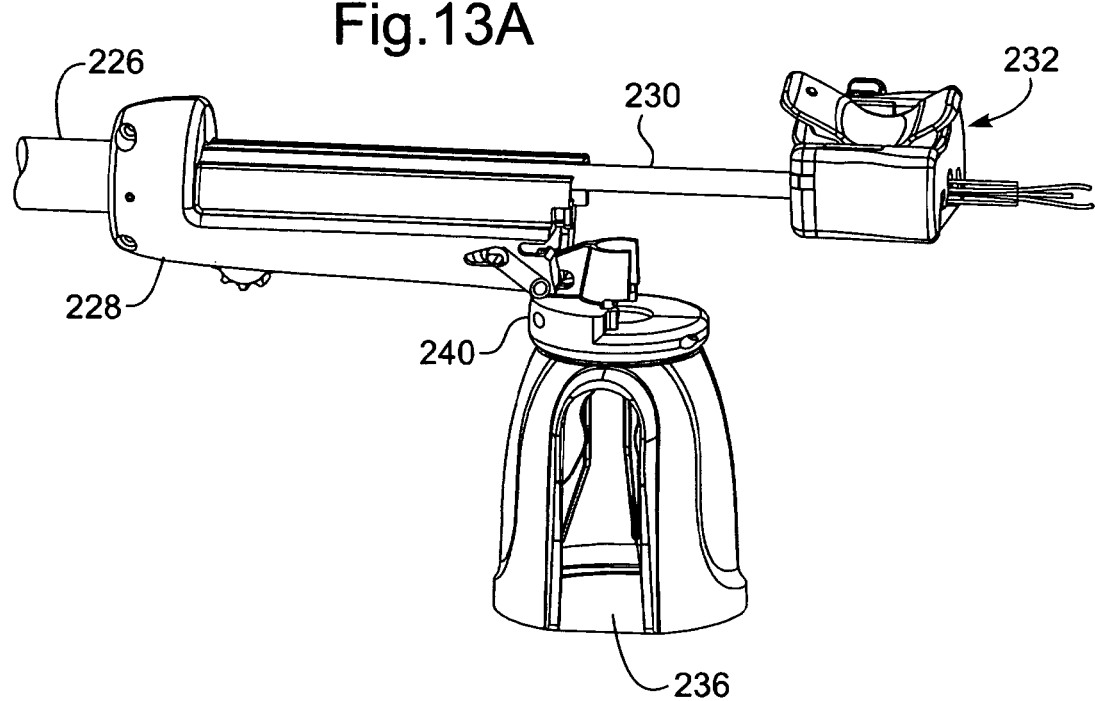
FIGS. 13A-13B are enlarged views of an alternative handle unit of the present invention similar to that shown in FIGS. 12A-12D, wherein an endoscope hood hinges away from a handle unit to permit coupling of a severing/securing tool thereto.
Figure 13B:
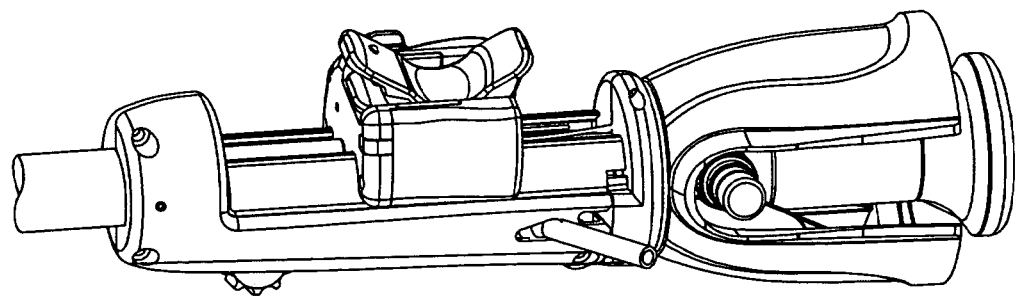
Figure 14A:
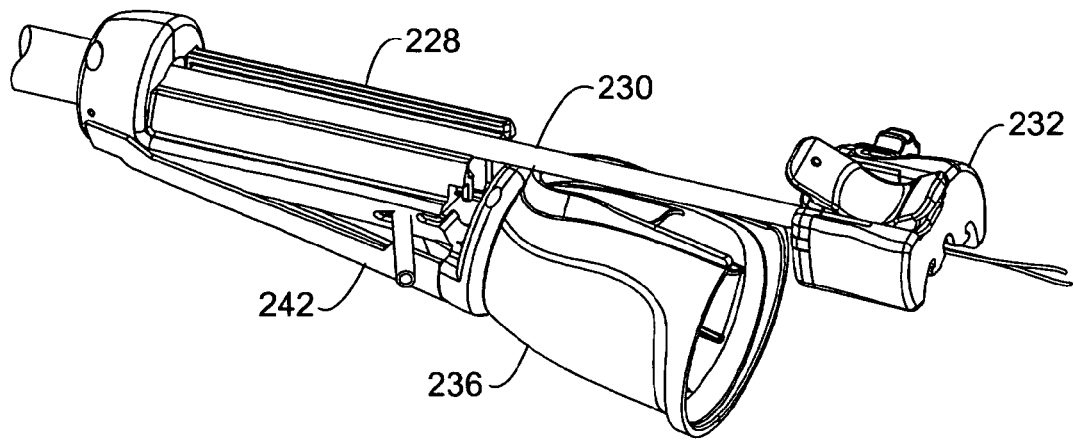
FIGS. 14A-14B are enlarged views of a further alternative handle unit of the present invention wherein an endoscope hood pivots away from a handle unit to permit coupling of a severing/securing tool thereto.
Figure 14B:
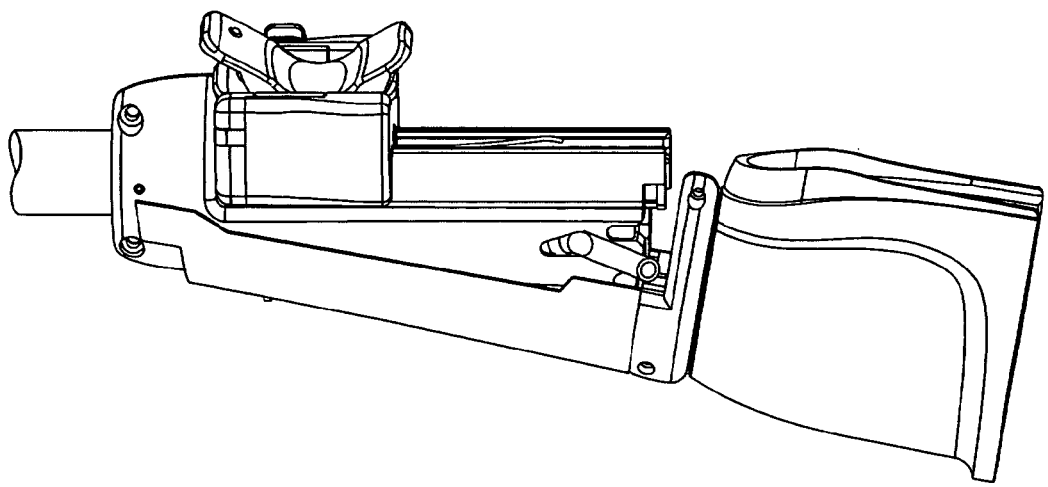

FIGS. 13A-13B and 14A-14B are enlarged perspective views of handle units similar to the handle unit shown in FIGS. 12A-12D, which also illustrate different means for displacing the endoscope-receiving hood 236 from the handle base 228 so as to permit insertion of the severing/securing tool. In both these embodiments, the tool shaft 230 projects through an aperture in the distal end of the handle base 228 and into the elongated cannula 226. The handle base 228 includes rails for receiving the tool carriage 232. In FIG. 13A the endoscope-receiving hood 236 attaches to the handle base 228 at a hinge member 240 and can be pivoted 90° away from a proximal end thereof to permit assembly of the severing/securing tool. In FIGS. 14A and 14B the endoscope-receiving said 236 attaches a handle base 228 at an elongated housing member 242 which can be pivoted away from a distal end thereof to permit assembly of the severing/securing tool. In both these embodiments, mechanisms for locking the endoscope-receiving hood 236 to the handle base 228 can be provided with detents, latches, etc.

Figure 15A:
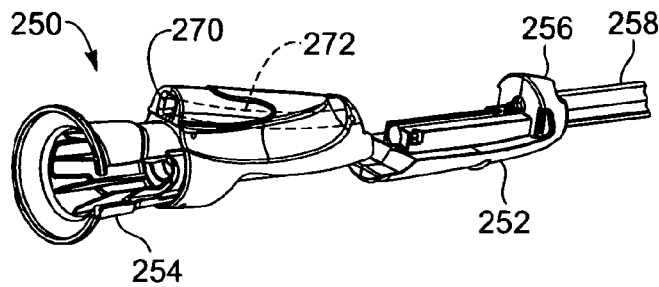
FIGS. 15A-15C are perspective views of a further modular alternative handle unit of the present invention that has an alternative sled/adapter that permits a handle base of the present invention to receive a conventional severing/securing tool.
Figure 15B:
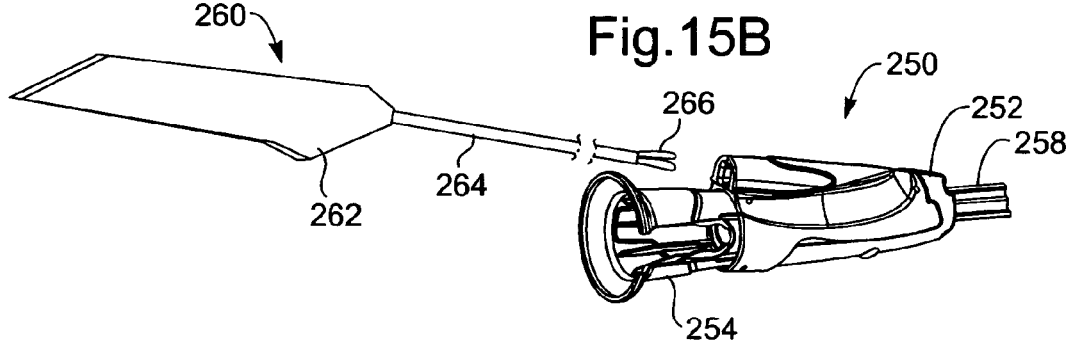
Figure 15C:
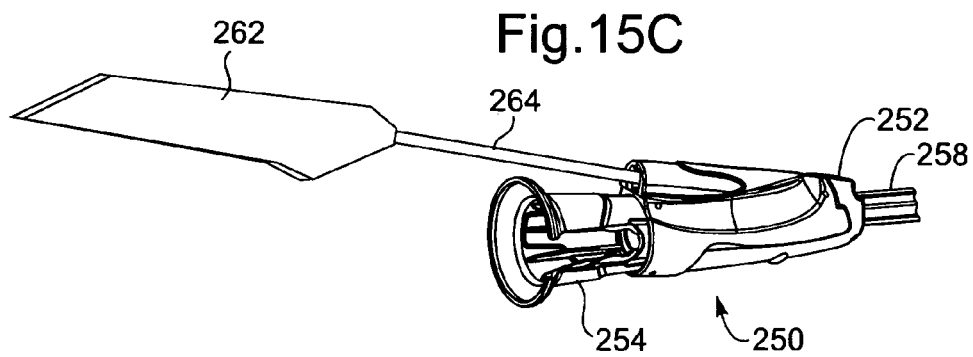

FIGS. 15A-15C show a slightly different variation of a modular handle unit 250 comprising a handle base 252 and handle sled 254. The handle base 252 may be identical to the handle base 50 described above with respect to FIGS. 2-8 and includes a distal flange 256 secured to an elongated cannula 258. The handle sled 254 includes structure for mating with the handle base 252, as seen in FIGS. 15B and 15C, and as described previously.

In contrast to the "integrated" or unitary handle units described above, the handle sled or adapter 254 adapts the handle base 252 so as to be capable of receiving a conventional severing/securing tool 260, such as a tissue welding instrument. The handle sled 254 provides an angled port 270 leading to a channel 272 through which the elongated shaft 264 of the severing/securing tool 260 may extend. The handle base 252 and handle sled 254 are aligned such that the elongated shaft 264 is guided through the distal flange 256 and harvesting tool cannula 258 as before. The final assembly as seen in FIG. 15C shows that some of the movement controls for the harvesting tools are located on the handle unit 250, while rotation of the severing/current tool 260 is accomplished by manipulating the handle 262 with a second hand.

Figure 15D:
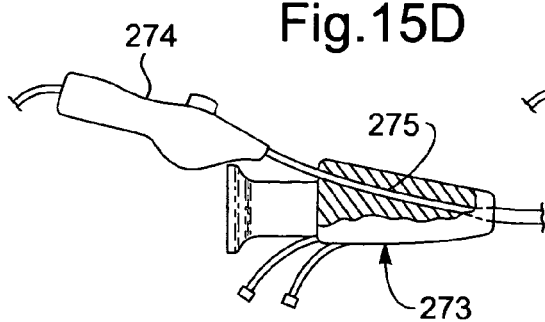
FIGS. 15D-15E are partially cutaway views of handle units similar to that shown in FIGS. 15A-15C and illustrating an alternative feature that ensures correspondence between a particular severing/securing tool and the handle unit.
Figure 15E:
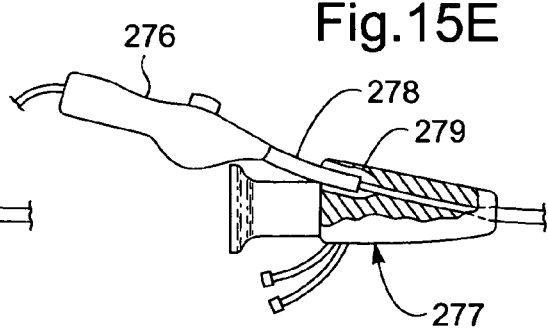

FIG. 15D is a schematic cutaway view of a handle unit 273 that is similar to the handle unit 250 shown in FIGS. 15A-15C. A constant diameter distal shaft of a severing/securing tool 274 is shown extending through a similarly sized channel 275 of the handle unit 273. In contrast, FIG. 15E illustrates an alternative arrangement which ensures correspondence between a severing/securing tool 276 and a handle unit 277. A proximal end of the shaft of the severing/securing tool 276 is provided with an enlarged section 278, and the mouth of a channel within the handle unit 277 includes a similarly shaped enlarged cavity 279. When coupling the severing/securing tool 276 with the handle unit 277, the enlarged section 278 closely fits within the cavity 279. The enlarged section 278 and cavity 279 are preferably cylindrical in shape such that the tool 276 can freely rotate with respect to the handle unit 277. However, the enlarged section 278 prevents use of the tool 276 with a handle unit 273 such as seen in FIG. 15D. It may be desirable to limit compatibility of the severing/securing tool 276 to assembly with the handle unit 277. It will of course be apparent to those of skill in the art that a variety of alternative cooperating structures are available to ensure compatibility between the tool 276 and handle unit 273, while restricting combination of the tool to the handle unit.

Severing/Securing Tool Rotation Mechanisms

In previous vessel harvesting systems, the severing/securing tool (e.g., bipolar scissors, tissue bisector, tissue welder) inserts separately from the cannula and associated handle and has an end effector that may be rotated by manually turning a proximal handle of the severing/securing tool. Tool rotation allows for greater flexibility and ease of positioning the end effector relative to tributaries to be dissected. Ideally, the end effector is oriented perpendicular to the tributary being cut. In the present invention, a mechanism for rotating the severing/securing tool and/or end effector is provided within an integrated handle unit, and is desirably designed to be operated by the thumb or finger of the same hand of the user that holds the handle unit. In addition, the tool rotation mechanism is desirably combined with means for axially extending the tool, and the combination of rotation and extension controls integrated into one small handle unit allows for more intuitive control of the tool. The rotation mechanisms of the present invention each include an actuator integrated with a handle unit, such as handle unit 24 disclosed above, and a transmission for converting movement of the actuator into rotation of the end effector.

In the exemplary embodiment of FIGS. 2-8, the handle unit 24 includes the axially movable carriage 56 and associated toggle switch 124 and thumbwheel 126. As explained above, displacing the carriage 56 along the handle unit 24 causes equal axial movement of the severing/securing tool 54 and its end effector 112 (FIG. 4E). Further, depression of the toggle switch 124 actuates the severing blade 116, and rotation of the thumbwheel 126 causes proportional rotation of the end effector 112. It should be understood that the three functions of axially displacing and also rotating the severing/securing tool, and actuating a severing blade can be accomplished by controls that are differently configured than the illustrated embodiment. For example, a slider instead of a carriage may be used to axially displace the tool, a thumbwheel may be connected to the severing blade, while a toggle switch or lever may be used as an actuator for the tool rotation. Indeed, a review of the following alternative embodiments of such actuators and connecting mechanisms will give the reader an idea of the vast number of permutations that are possible, and the invention should not be considered limited to those embodiments that are illustrated and described.

Referring now to the partial, cutaway perspective view of FIGS. 16A-16B, an exemplary assembly of manual control elements to remotely control movement of an end effector of a severing/securing tool is shown. A handle unit 280 is shown with a right-side segment removed in FIG. 16B to illustrate the assembly therein. Each of the left-side and right-side segments of the handle unit 280 include longitudinal rails 282 that engage mating slots 284 in the lower side edges of a tool carriage 286 to captivate the carriage and facilitate longitudinal sliding thereof with respect to the handle unit 280.

A rotation actuator 290 mounted on the tool carriage 286 to pivot generally about a longitudinal axis supports a rocking element 292 that in turn pivots about axis 294. Pivoting of the rocking element 292 moves an extension flange 296 depending underneath fore and aft generally along the axis of the handle unit 280. The flange 296 is linked to an actuating rod 298 that extends distally through a severing/securing tool shaft 300 to an end effector (not shown).

Because the rotation actuator 290 is fixed with respect to the tool shaft 300, pivoting of the actuator in the direction of arrows 302 causes equivalent rotation of the tool shaft 300 about its axis. That is, there is no intervening "transmission," but instead the transmission is a physical connection between the actuator 290 and tool shaft 300. Furthermore, linear movement of the carriage 286 in either direction 304 causes linear movement of the tool shaft 300, as indicated by double-headed arrow 306. Finally, actuation of the rocking element 292 translates the actuating rod 298 back-and-forth, which may be connected to a vessel severing blade.

A slider 310 is captivated along a longitidinal rail 312 that is formed in the lower portion of the handle unit 280. The slider 310 may be linked to another actuating rod (not shown) that ultimately controls extension and retrieval of a vessel cradle. It is therefore clear that as the tool carriage 286 is mounted on the handle unit, the entire assembly is integrated for one-handed operation by the user.

Figure 17A:
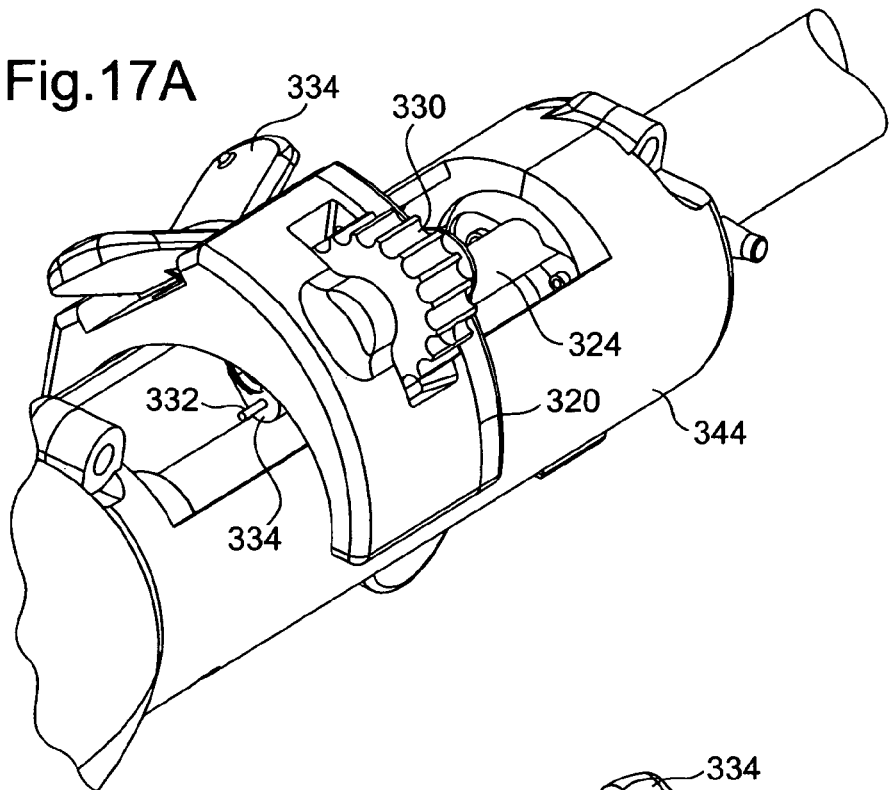
FIGS. 17A-17D are perspective and partially cutaway views of an alternative severing/securing tool actuation mechanism.
Figure 17B:
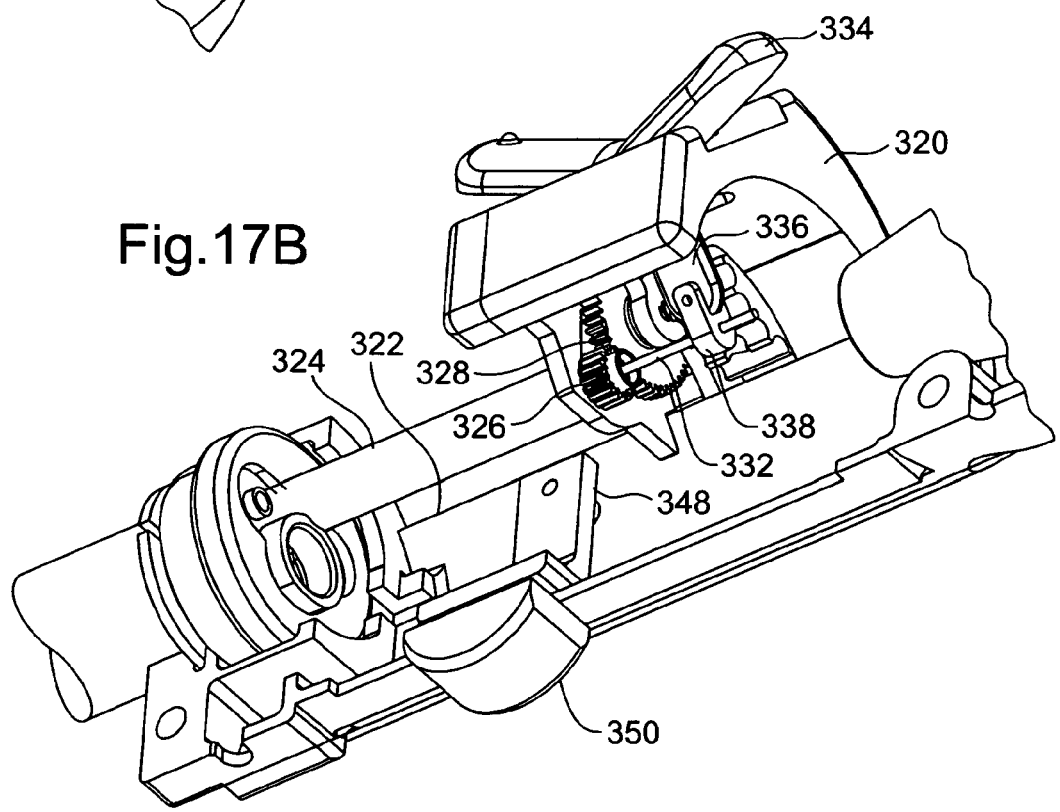
Figure 17C:
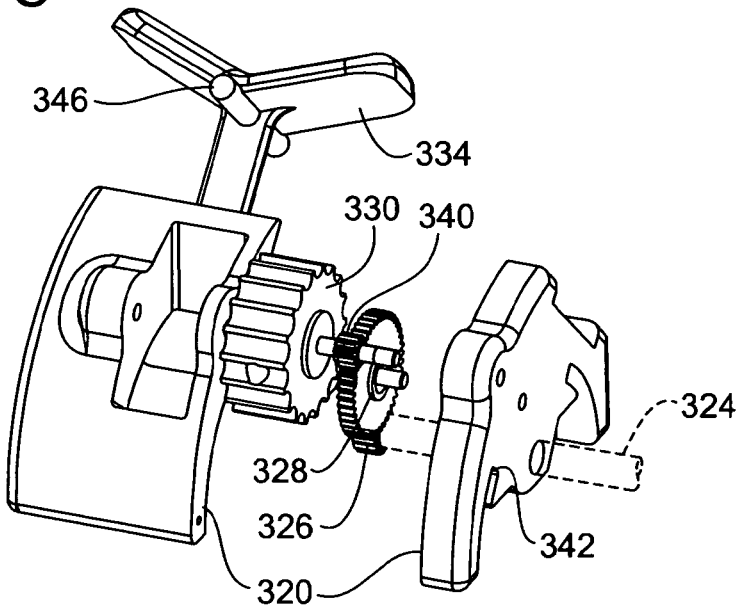
Figure 17D:
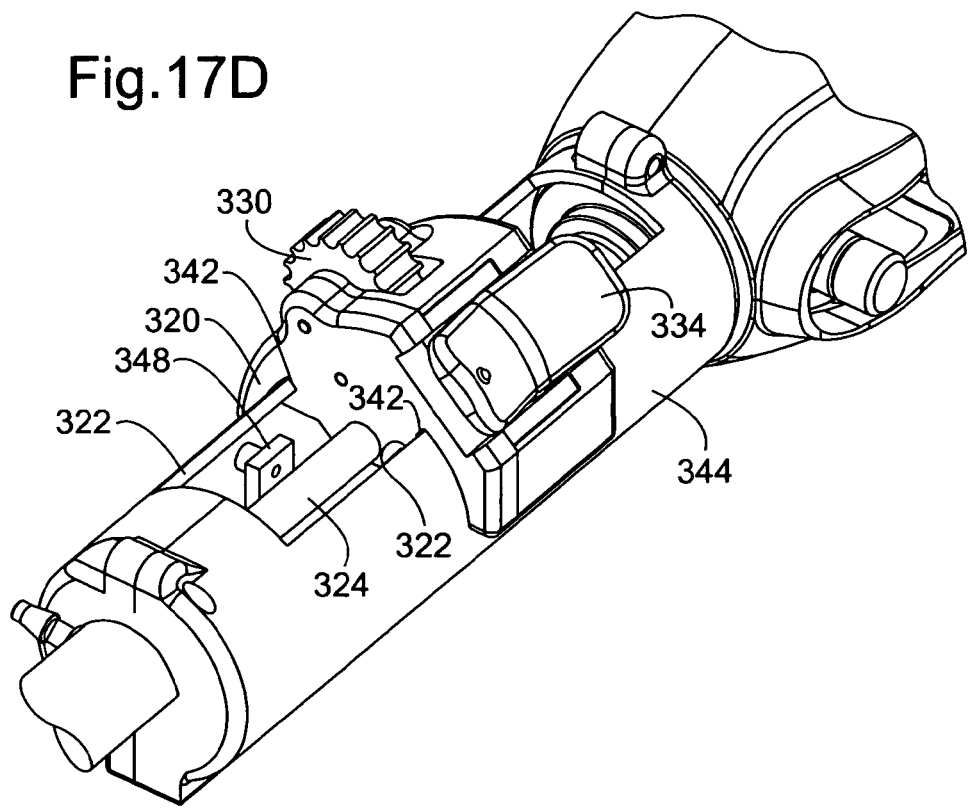

FIGS. 17A and 17B are side and underside cutaway perspective views of another embodiment of manual control elements for actuating severing/securing tool end effectors. The underside view of FIG. 17B omits an endoscope from the assembly for clarity of illustration. In this embodiment, a carriage 320 slides along longitudinal rails 322 and is attached to a severing/securing tool shaft 324 for corresponding axial translation. The outer housing of the tool shaft 324 is coupled for rotation with respect to the carriage 320, and has fixed thereon a pinion gear 326 that meshes with an idler gear 328 rotatable on the carriage 320. Referring additionally to FIGS. 17C and 17B, a thumbwheel 330 supported on the carriage 320 carries a pinion gear 340 that meshes with the idler gear 328. Accordingly, the tool shaft 324 rotates in response to rotation of the thumbwheel 330, or "actuator." The "transmission" in this embodiment comprises a gear train. The illustrated embodiment shows the thumbwheel 330 and associated pinion gear 340 journaled for rotation about an axis that is parallel to the axis of the tool shaft 324 and associated pinion 326, and also parallel to the axis of rotation of the idler gear 328. Alternative configurations could include bevel gears, miter gears, or crown gears whose axes of rotation are non-parallel to the axis of the tool shaft pinion 326.

An actuating rod 332 is linked to a rocking element 334 that is supported to rotate about a lateral pivot (not shown) on the carriage 320. Specifically, the rocking element 334 includes a flange 336 depending therefrom that interacts with a hinge member 338 fixed on the actuating rod 332. The ends of the carriage 320 include guide slots 342 that mate with the longitudinal rails 322 to slidably support the carriage on the handle unit 344. The proximal end of a severing/securing tool (such as a tissue transector, or scissors) is rotatably supported but longitudinally constrained within the carriage 320. The carriage 320 supports a lateral pivot 346 for the rocking element 334. As illustrated in the partial perspective view of FIG. 17C, the carriage 320 slides along the rails 322 at the edges of the longitudinal slot in the handle unit 344 to extend and retrieve the severing/securing tool. A lever arm 348 attached to a slider 350 (FIG. 17B) in the lower portion of the handle unit 344 may be linked (not shown) to another surgical instrument such as a vessel cradle.

Thus, longitudinal sliding back and forth of the carriage 320 axially extends and retracts the tool shaft 324, rotation of the thumbwheel 330 angularly rotates the tool shaft about its longitudinal axis, and moving the rocking element 334 fore and aft actuates the end effector at the distal end of the tool shaft.

FIGS. 18A-18F are schematic views of alternative severing/securing tool rotation mechanisms. These schematics are included to illustrate the range of possible mechanical structures for imparting rotational/angular motion to a tool shaft of a severing/securing tool, which rotates the end effector thereof. These mechanisms are desirably incorporated into an "integrated" handle unit of a vessel harvesting system of the present invention, as detailed above with respect to the exemplary embodiment of FIGS. 17A-17D. In general, each of these alternative rotation mechanisms includes an actuator integrated with a handle unit, such as handle unit 24 disclosed above, and a transmission for converting movement of the actuator into rotation of the end effector.

In FIG. 18A, a tool shaft 360 of a severing/securing tool (equivalent to the aforementioned tool shaft 324 of FIGS. 17A-17D) is journaled for rotation (e.g., within a sliding carriage, as previously described herein) and carries a pinion gear 362 thereon meshed with a rack gear 364. Such rack gear 364 may be mounted for lateral movement within a carriage (e.g., carriage 320 of FIGS. 17A-17D) that is mounted for longitudinal movement relative to a harvesting tool cannula (not shown). The angular rotation of the tool shaft 360 about its longitudinal axis may be controlled via lateral movement of the rack gear 364. An actuating rod 366 for an end effector of the severing/securing tool is seen passing through the center of the tool shaft 360.

In another embodiment of the present invention as shown in the pictorial illustration of FIG. 18B, a tool shaft 360 of a severing/securing tool attaches to a bell crank 370 that supports an eccentric pin 372. The eccentric pin 372 engages a slot 374 formed within a shuttle 376 that in turn is mounted (e.g., on the sliding carriage) for lateral movement relative to the longitudinal axis of the tool shaft. Lateral movement of the shuttle 376 translates into angular orientation of the tool shaft 360 about its longitudinal axis. It will be apparent to those of skill in the art that the shuttle 376 may be actuated in a number of ways, including, for example, connecting it directly to a thumb slider.

In another embodiment of the present invention as illustrated in FIG. 18C, a pinion gear 380 on a severing/securing tool shaft 360 meshes with a ring gear 382 that is configured as a thumbwheel carried by a sliding carriage. The angular orientation of the tool shaft 360 is therefore controlled by rotation of the thumbwheel/ring gear 382.

In a bell-crank amplifier embodiment shown in the schematic illustration of FIG. 18D, the severing/securing tool shaft 360 attaches to a lever arm 390. A crank 392 is journaled for rotation about a longitudinal axis that is substantially aligned with, and displaced from, the longitudinal axis of the tool shaft 360, and a linkage 394 translates side-to-side movement of the crank 392 to angular orientation of the tool shaft 360 about its longitudinal axis. Those of skill in the art will understand that various such lever systems may be similarly incorporated. A small amount of user rotational input to the crank 392 amplifies into a greater amount of lever arm 390 rotation, and thus tool shaft rotation. Various ways to amplify the input rotation are possible, and such amplification enables more rapid re-orientation of the end effector of the tool shaft during the vessel harvesting procedure.

In another embodiment of the present invention as illustrated in FIG. 18E, a belt 400 mechanically couples a drive pulley 402 and a driven pulley 404, that is in turn connected to a severing/securing tool shaft (not shown). In one direction of rotation, one side of the belt in tension winds upon the driven pulley 404 while the other side unwinds. When the direction of rotation is reversed, the first side of the belt now unwinds while the second side is in tension. The belt 400 may be fabricated from thread, metal cable, or metal/plastic/fabric belt material. Further, rotation of the drive pulley 402 such as by an associated thumbwheel 406 (which could be a lever or toggle) rotates the driven pulley 404 through a larger angular rotation because of the relative sizes of the pulleys. Alternatively, the drive pulley 402 may be smaller than the driven pulley 404 so that the severing/securing tool shaft rotates less than the thumbwheel, which provides greater precision in positioning of the end effector and also provides a greater mechanical advantage in turning.

Similarly, as illustrated in FIG. 18F, a severing/securing tool shaft 410 may be coupled via a flexible strand 412 to a larger diameter drive shaft 414 and associated thumbwheel 416. Rotation of the thumbwheel 416 and drive shaft 414 winds and unwinds the flexible strand 412 about the tool shaft 410 and thus imparts greater angular displacement thereto. These pulley system embodiments of the present invention thus conveniently amplify rotational movement of the driven tool shafts in response to rotational movement of the respective drive shafts and thumb wheels.

FIG. 19 is a perspective exploded view of an exemplary structure integrated into a thumbwheel 420 for limiting rotation of a severing/securing tool shaft (not shown) within the system. It is often desirable to limit the amount of rotation of a tool shaft because it typically carries wires to power an end effector such as a bipolar bisector, for example, as described herein with reference to FIGS. 2-8. Limiting rotation of the tool shaft thus reduces the risk of twisting or otherwise stressing the wires to failure. In addition, the structure for limiting the angular rotation of the tool shaft/end effector directly limits movement of the actuator/thumbwheel 420, and only indirectly limits rotation of the tool shaft, which avoids stressing the gears that couple the thumbwheel to the tool shaft. That is, the structure for limiting the angular rotation of the tool shaft/end effector does not act through the transmission, but rather directly on the actuator/thumbwheel 420.

The thumbwheel 420 attaches to and rotates a shaft 421 parallel to the severing/securing tool shaft that further includes a drive gear 422 meshed with a driven gear (such as gear 326 shown in FIG. 17C) arranged to rotate a tool shaft. Preferably, due to the relative sizes of the gears, angular rotation of the thumbwheel 420 produces greater angular rotation of the tool shaft. A cam washer 428 rotates freely about the shaft 421 and includes a cam lobe or stop pin 426 projecting on both sides thereof and radially located to fit within a cavity 427 in the thumbwheel 420. As the thumbwheel 420 turns, an integral radial spoke 424 engages the closer pin 426 so as to rotate the cam washer 428. The farther pin 426 eventually engages a stop or fixed abutment 429 formed, for example, on a handle unit (such as handle unit 24 in FIGS. 2-8), thus preventing further rotation of the thumbwheel 420. Advantageously, this separate stop mechanism avoids unnecessary reaction stresses upon the meshed gears that might otherwise be imposed by directly inhibiting excessive rotation of the tool shaft. Indeed, the gears are often molded plastic susceptible to stripping.

Desirably, the thumbwheel 420 is free to rotate about an angle of greater than 360°, or one turn, and slightly less than 720°, or two turns. In this way, the end effector of the connected severing/securing tool has full range of rotational motion, but its rotation is limited to prevent damage to the control wires/rods. In an alternative embodiment, the thumbwheel stop mechanism constrains the end effector to rotate less than one full turn, for example about 180°, in which case the center of the range of thumbwheel angular rotation may be synchronized to a particular position of the end effector. For instance, the end effector may be oriented in a reference plane of 0° at the central position of the thumbwheel, wherein rotation of the thumbwheel turns the end effector in either direction from the reference plane.

Referring now to FIGS. 19A-19H, a number of alternative embodiments of freely-rotatable cam washers 428 are disclosed. The cam washers 428 possess peripheral cam lobes or stop tabs 430 instead of protruding pins 426 as in FIG. 19. When utilized in the thumbwheel stop mechanism in FIG. 19, the radial spoke 424 in thumbwheel 420 contacts the interfering stop tab 430 and a second tab contacts a feature in the handle unit, such as the abutment 429 in FIG. 19. In all but one of these alternative embodiments, there are two stop tabs, some of which are bends in opposite directions, and some that are perpendicular to one another. For example, in FIG. 19A the two tabs 430 extend in opposite directions, much like the stop pin 426 of the cam washer 428 of FIG. 19. In contrast, FIG. 19B illustrates one bent tab 430 and one that remains in the plane of the cam washer 428. It will be understood by those of skill in the art that the thumbwheel 420 may be arranged to contact either of the stop tabs, with a complementary feature provided on the handle unit to interfere with the other tab. In a slight variation, FIG. 19C shows a cam washer 428 with only one bent tab 430. The thumbwheel 420 may contact the bent portion of the tab 430, while a straight portion 431 is arranged to contact a projection (not shown) of the handle unit.

As will be understood by one of skill in the art, multiple cam washers 428 may be stacked on top of each other for a greater degree of rotation before stopping. If only one cam washer is used, it is desirable to place the two cam lobes on the same quadrant to reduce the possibility of skewing the cam washer and therefore jamming it within the mechanism. Specifically, the cam washers 428 of FIGS. 19 and 19C-19H include cam lobes that are either at the same circumferential location or within approximately 90° with respect to one another. Some of the illustrated cam washers 428 are available off-the-shelf so as to reduce cost. Preferably, the various elements of the severing/securing tool rotation mechanism, including the cam washers 428, are molded of plastic.

It will also be appreciated by those of skill in the relevant art that various modifications or changes may be made to the examples and embodiments described without departing from the intended scope of the invention. In this regard, the particular embodiments of the invention described herein are to be understood as examples of the broader inventive concept disclosed.

What is claimed is:

1. A vessel harvesting system comprising:
   a handle;
   a shaft member extending distally from the handle, wherein the shaft member comprises a proximal end and distal end;
   a first tool extending distally from the shaft member distal end, wherein the first tool comprises a tool shaft and an end effector configured to manipulate tissue; and
   a control system connected to the first tool and adapted to axially extend the first tool beyond the distal end of the shaft member along a first pathway and adapted to move the first tool along a second pathway different than the first pathway, and wherein the control system comprises:
      a carriage movable along a portion of the handle to allow for movement of the first tool along the first pathway; and
      a first actuator movably mounted to the carriage to allow for movement of the first tool along the second pathway.

2. The vessel harvesting system of claim 1, wherein the first tool is rotated about a longitudinal axis of the shaft member when moved along the second pathway.

3. The vessel harvesting system of claim 1, wherein the first actuator is a thumbwheel rotatably mounted to the carriage.

4. The vessel harvesting system of claim 1, wherein the control system further comprises a second actuator movably mounted to the carriage for actuating the end effector.

5. The vessel harvesting system of claim 4, wherein the end effector comprises a blade and wherein the second actuator is capable of actuating the blade.

6. The vessel harvesting system of claim 4, wherein the second actuator comprises a rocking element mounted to the carriage for actuating the end effector.

7. The vessel harvesting system of claim 1, wherein the end effector comprises an electrode.

8. The vessel harvesting system of claim 1, further comprising a retractor configured for engaging tissue and capable of being axially extended distally with respect to the shaft member distal end.

9. The vessel harvesting system of claim 1, wherein the handle comprises one or more rails along which the carriage slides for axially extending the first tool.

10. The vessel harvesting system of claim 1, wherein the first actuator is pivotally mounted on and configured to rotate about a surface of the carriage and wherein the rotation of the first actuator induces equivalent rotation of the end effector of the first tool along the second pathway.

11. A vessel harvesting system of claim 10,
wherein the first tool is slidably positioned within a lumen defined in the shaft member and wherein the shaft member is further configured to receive an endoscope located adjacent to the first tool.

12. The vessel harvesting system of claim 1, wherein the first actuator is operatively associated with the first tool such that rotational movement of the first actuator induces movement of the first tool along the second pathway.

13. A vessel harvesting system comprising:
a handle;
a shaft member extending distally from the handle, wherein the shaft member comprises a proximal end and distal end;
a first tool extending distally from the shaft member distal end, wherein the first tool comprises a tool shaft and an end effector configured to manipulate tissue; and
a control system connected to the first tool and adapted to axially extend the first tool in a first direction along a longitudinal axis of the shaft member and adapted to move the first tool in a second direction different than the first direction, wherein the control system comprises:
a carriage movable along a portion of the handle; and
an actuator pivotally mounted on and adapted to rotate about a surface of the carriage for rotating the first tool in the second direction.

14. The vessel harvesting system of claim 13, wherein the carriage is operatively associated with the first tool such that movement of the carriage along the portion of the handle imparts axial movement of the first tool.

15. The vessel harvesting system of claim 13, wherein the system further comprises one or more rails positioned between the handle and carriage and wherein the carriage slides along the one or more rails to axially extend the first tool.

16. A method for harvesting a first vessel involving the use of a surgical tool system, the surgical tool system comprising a handle, a shaft member extending distally from the handle, a first tool extending distally from a distal end of the shaft member for manipulating tissue, and a control system comprising a carriage movable along a portion of the handle for positioning the first tool and an actuator movably mounted to the carriage, the method comprising the steps of:
actuating the control system to axially extend the first tool beyond the shaft member distal end along a first pathway;
actuating the control system to move the first tool along a second pathway different than the first pathway;
severing a branch vessel of the first vessel using the first tool; and
harvesting the first vessel.

17. The method of claim 16, wherein the step of actuating the control system to move the first tool along the second pathway comprises rotating the actuator coupled to the carriage, thereby causing rotation of the first tool relative to the shaft member.

18. The method of claim 16, wherein the step of actuating the control system to axially extend the first tool comprises sliding the carriage of the control system along the handle.

19. The method of claim 18, wherein the step of actuating the control system to move the first tool along a second pathway comprises rotating the actuator coupled to the carriage to rotate the first tool relative to the shaft member.

20. The method of claim 16, further comprising the step of using the first tool to coagulate or transect the branch vessel.

\* \* \* \* \*